(12) United States Patent
Dealwis

(10) Patent No.: US 12,011,432 B2
(45) Date of Patent: Jun. 18, 2024

(54) METHOD OF MODULATING RIBONUCLEOTIDE REDUCTASE

(71) Applicant: CASE WESTERN RESERVE UNIVERSITY, Cleveland, OH (US)

(72) Inventor: Chris Dealwis, Highland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 583 days.

(21) Appl. No.: 17/260,998

(22) PCT Filed: Jul. 18, 2019

(86) PCT No.: PCT/US2019/042338
§ 371 (c)(1),
(2) Date: Jan. 16, 2021

(87) PCT Pub. No.: WO2020/018747
PCT Pub. Date: Jan. 23, 2020

(65) Prior Publication Data
US 2021/0299095 A1    Sep. 30, 2021

Related U.S. Application Data

(60) Provisional application No. 62/700,050, filed on Jul. 18, 2018.

(51) Int. Cl.
| | | |
|---|---|---|
| *A61K 31/404* | (2006.01) | |
| *A61K 31/15* | (2006.01) | |
| *A61K 31/341* | (2006.01) | |
| *A61K 31/381* | (2006.01) | |
| *A61K 31/426* | (2006.01) | |
| *A61K 31/4406* | (2006.01) | |
| *A61K 31/4412* | (2006.01) | |
| *A61K 31/52* | (2006.01) | |
| *A61K 45/06* | (2006.01) | |
| *A61P 35/00* | (2006.01) | |

(52) U.S. Cl.
CPC ............ *A61K 31/404* (2013.01); *A61K 31/15* (2013.01); *A61K 31/341* (2013.01); *A61K 31/381* (2013.01); *A61K 31/426* (2013.01); *A61K 31/4406* (2013.01); *A61K 31/4412* (2013.01); *A61K 31/52* (2013.01); *A61K 45/06* (2013.01); *A61P 35/00* (2018.01)

(58) Field of Classification Search
None
See application file for complete search history.

(56) References Cited

U.S. PATENT DOCUMENTS 9,889,129 B2    2/2018    Dealwis
2015/0291562 A1    10/2015    Crew et al.

FOREIGN PATENT DOCUMENTS

WO    2017/100644 A1    6/2017

OTHER PUBLICATIONS

Bouhadir et al. (Org. Commun. 10:4 259-272, 2017).*

* cited by examiner

*Primary Examiner* — Bong-Sook Baek
(74) *Attorney, Agent, or Firm* — TAROLLI, SUNDHEIM, COVELL & TUMMINO, LLP

(57) ABSTRACT

A method of modulating ribonucleotide reductase activity in a neoplastic cell includes administering to the cell an amount of a hydrazone or hydrazine ribonucleotide reductase modulator (RRmod), the amount being effective to inhibit neoplastic cell growth.

8 Claims, 11 Drawing Sheets

Fig. 7

METHOD OF MODULATING RIBONUCLEOTIDE REDUCTASE

RELATED APPLICATION

This application claims priority from U.S. Provisional Application No. 62/700,050, filed Jul. 18, 2018, the subject matter of which is incorporated herein by reference in its entirety.

GOVERNMENT FUNDING

This invention was made with government support under GM100887 and CA100827 awarded by the National Institutes of Health. The government has certain rights in the invention.

FIELD OF THE INVENTION

The present invention relates to selective hydrazone and hydrazine modulators of ribonucleotide reductase (RR) and to methods of using such modulators for therapeutic applications.

BACKGROUND

Ribonucleotide reductase (RR) is a highly regulated enzyme which catalyzes the de novo dNTP synthesis pathway that is ubiquitously present in human, bacteria, yeast, and other organisms. RR plays a crucial role in de novo DNA synthesis by reducing ribonucleoside diphosphates to 2'-deoxy ribonucleoside diphosphates and maintains balanced pools of deoxynucleoside triphosphates (dNTPs) in the cell.

RRs are divided into three classes, I to III, based on the method of free-radical generation. All eukaryotic organisms encode a class I RR, consisting of an αnβn multi-subunit protein complex, in which the minimally active form is α2β2. The α or RR1 (large) subunit contains the catalytic (C-site) and two allosteric sites, while the β or RR2 subunit houses a stable tyrosyl free radical that is transferred some 35 Å to the catalytic site to initiate radical-based chemistry on the substrate.

RR is regulated transcriptionally, allosterically and, in the yeast *S. cerevisiae*, RR is further regulated by subunit localization and by its protein inhibitor Sml1. In mammalian cells, RR activity is also controlled by the RR2 levels. Consistent with the varying RR2 levels, dNTP pools also vary with the phases of the cell cycle, reaching the highest concentration during S-phase. RR is regulated by an intricate allosteric mechanism. The two previously described allosteric sites of RR are the specificity site (S-site), which determines substrate preference, and the activity site (A-site), which stimulates or inhibits RR activity depending on whether ATP or dATP is bound.

RR is directly involved in neoplastic tumor growth, metastasis, and drug resistance. The proliferation of cancer cells requires excess dNTPs for DNA synthesis. Therefore, an increase in RR activity is necessary as it helps provide extra dNTPs for DNA replication in primary and metastatic cancer cells. Because of this critical role in DNA synthesis, RR represents an important target for cancer therapy. However, existing chemotherapies that target ribonucleotide reductase are nucleoside-based analogs. Hence, they are promiscuous, leading to nonspecific binding of other nucleoside binding proteins which results in unwanted side effects. Therefore, there is a need for compositions and methods for specifically targeting and inhibiting RR activity in neoplastic cells in the treatment of neoplastic disorders.

SUMMARY

Embodiments described herein relate to compounds and methods of modulating ribonucleotide reductase activity in a neoplastic cell. In some embodiments, the method can include administering to a neoplastic cell an amount of a ribonucleotide reductase modulator (RRmod) effective to inhibit neoplastic cell growth.

In some embodiments, the RRmod can include a compound having the structure of formula (I):

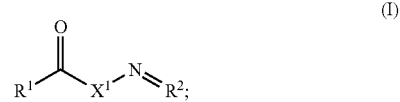

or a pharmaceutically acceptable salt, tautomer, or solvate thereof, wherein:

$X^1$ is NH or O; and $R^1$ and $R^2$ are independently selected from the group consisting of substituted or unsubstituted aryl, a substituted or unsubstituted heteroaryl, a substituted or unsubstituted cycloalkyl, and a substituted or unsubstituted heterocyclyl.

In some embodiments, $R^2$ is not a hydroxynaphthalenyl or an indole.

In some embodiments, $R^1$ is selected from the group consisting of:

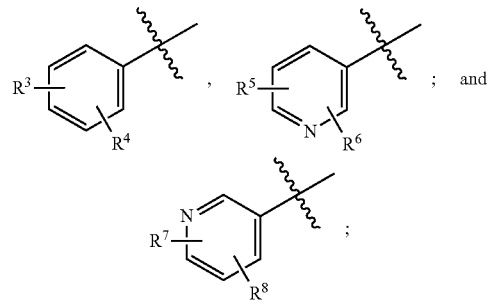

wherein each of $R^3$, $R^4$, $R^5$, $R^6$, $R^7$, and $R^8$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl) 3, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, and combinations thereof.

In still other embodiments, $R^1$ is selected from the group consisting of:

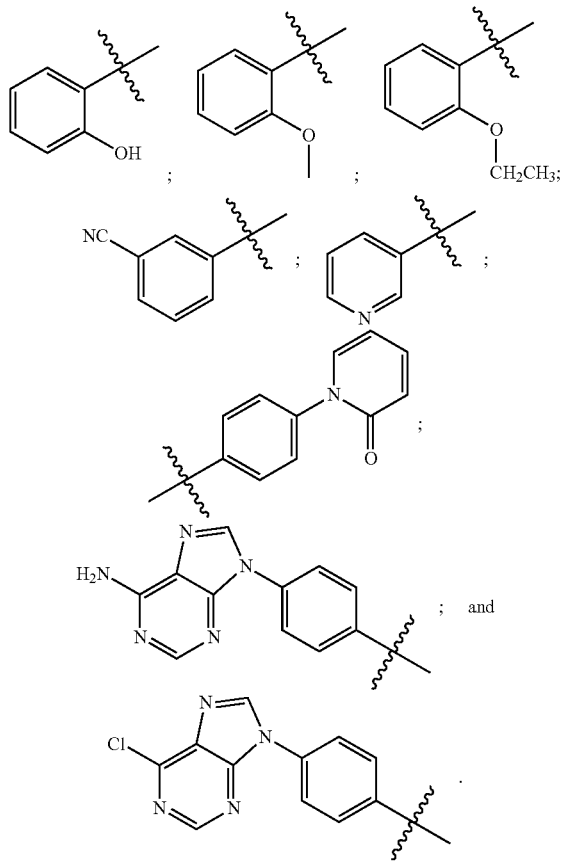

In some embodiments, $R^2$ is selected from the group consisting of:

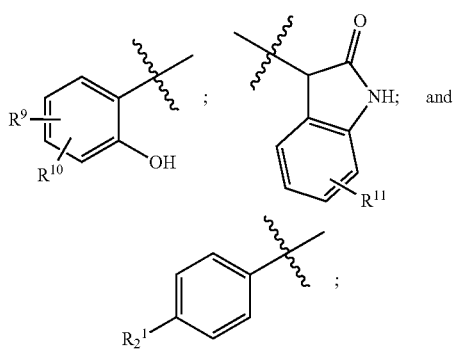

wherein each of $R^9$, $R^{10}$, $R^{11}$ and $R^{12}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, and combinations thereof.

In some embodiments, $R^2$ is selected from the group consisting of:

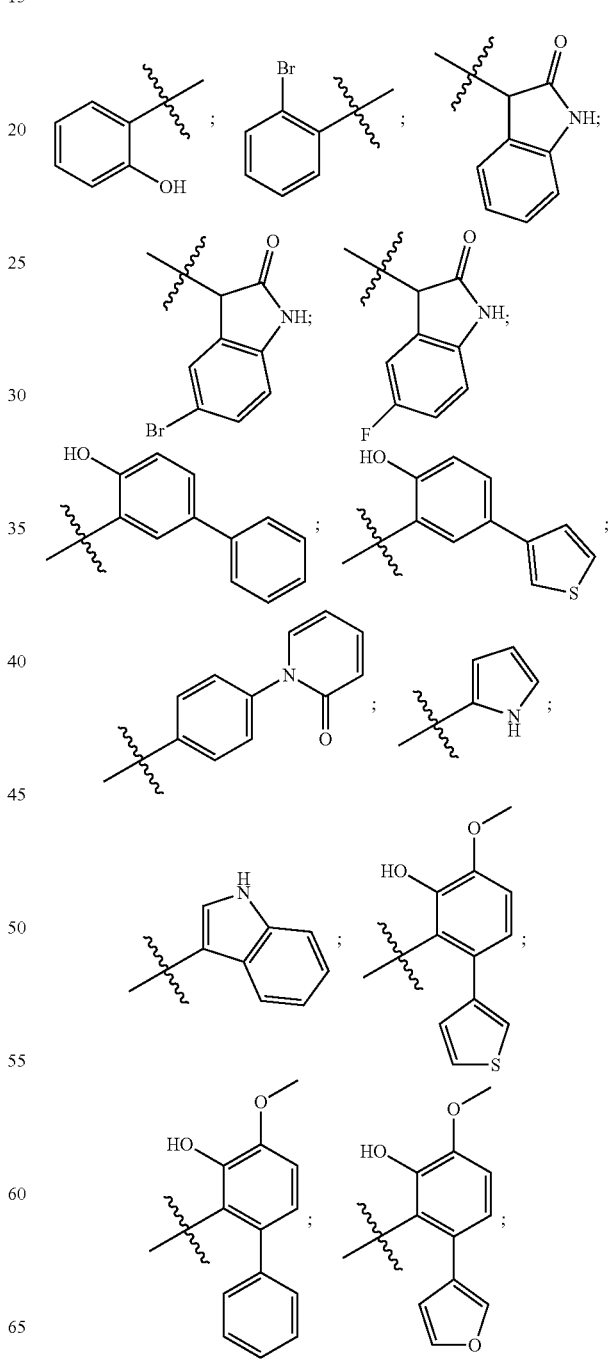

-continued

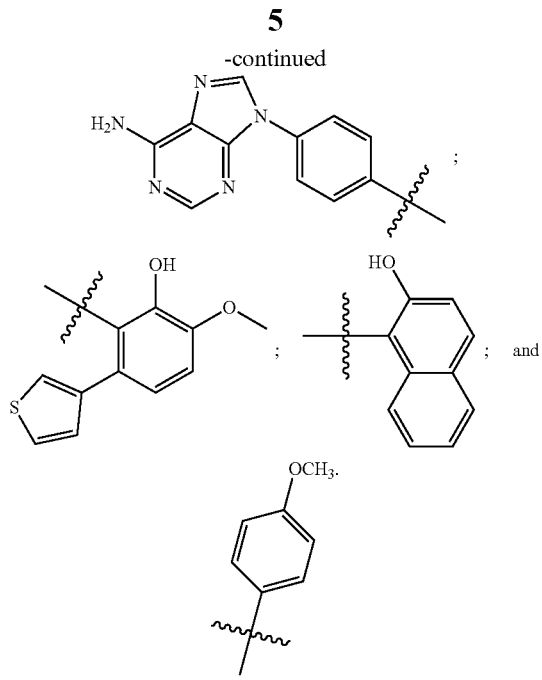

In some embodiments, the RRmod can include a compound having the formula (II):

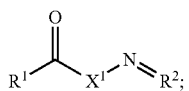
(II)

or a pharmaceutically acceptable salt, tautomer, or solvate thereof, wherein:

$X^1$ is NH or O;

$R^1$ is selected from the group consisting of:

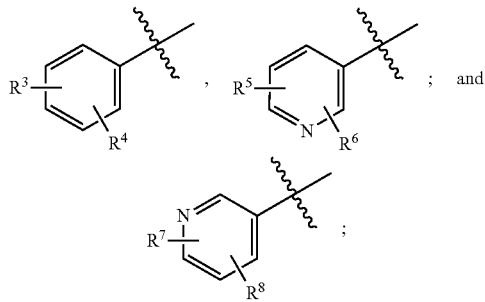

$R^2$ is selected from the group consisting of:

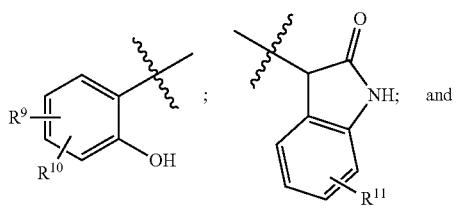

-continued

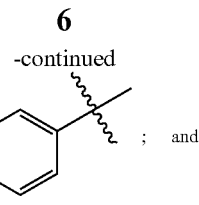

each of $R^3$, $R^4$, $R^5$, $R^6$, $R^7$, $R^8$, $R^9$, $R^{10}$, $R^{11}$, and $R^{12}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{26}$ aryl, heteroaryl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{26}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{26}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{26}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{26}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, and combinations thereof.

In certain embodiments, an RRmod having the structure of formula (I) or formula (II) can be selected from the group consisting of:

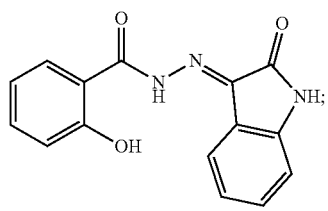

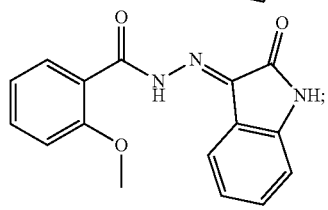

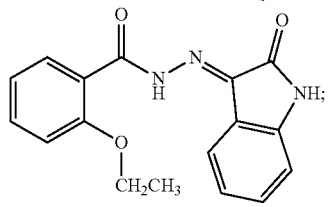

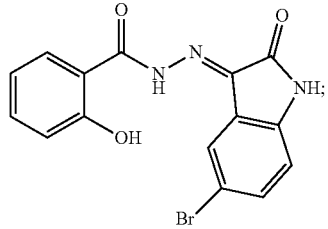

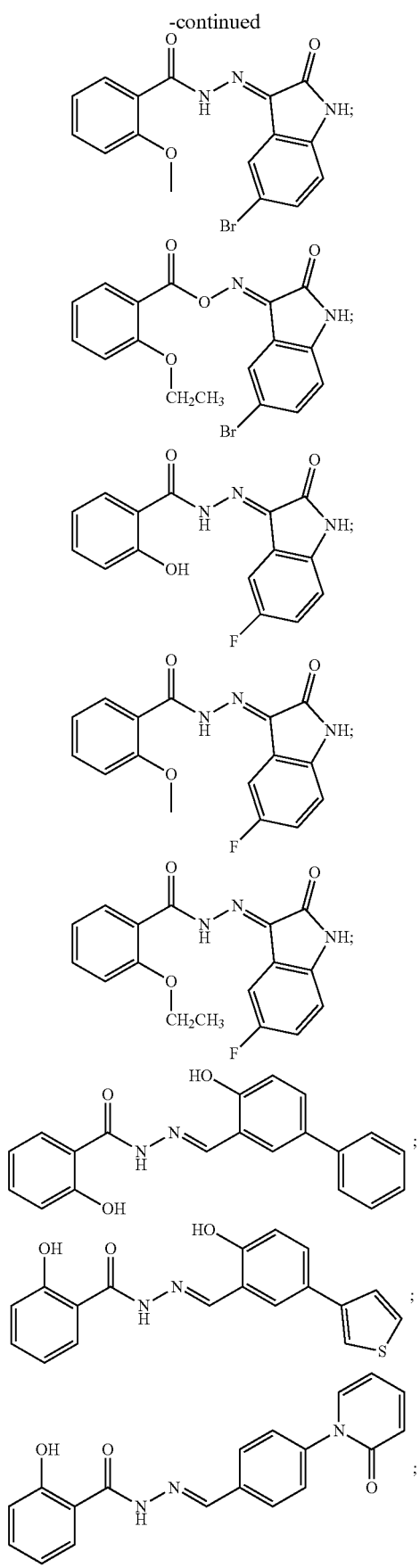
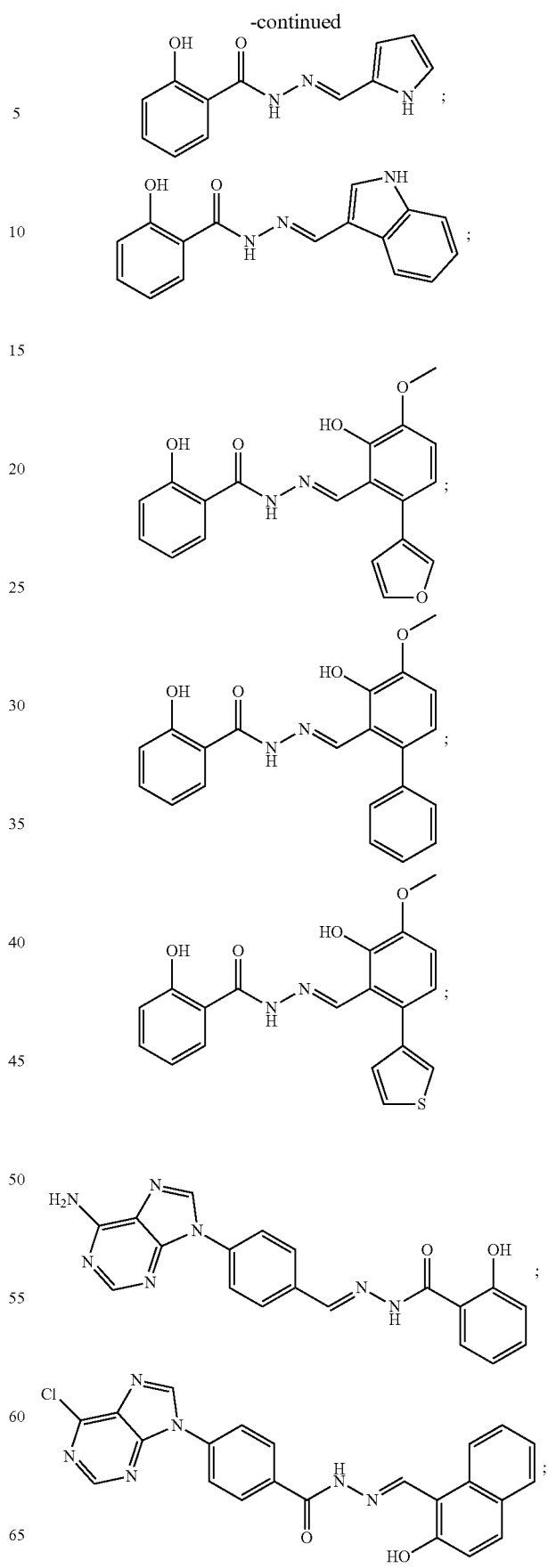

-continued

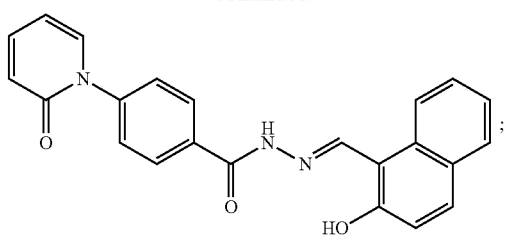

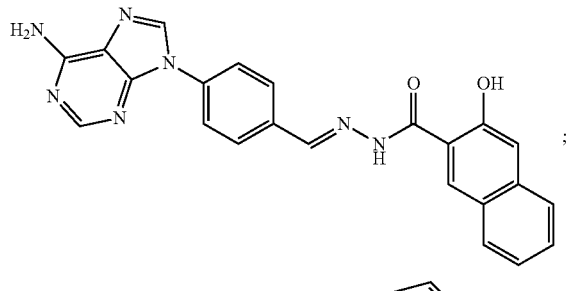

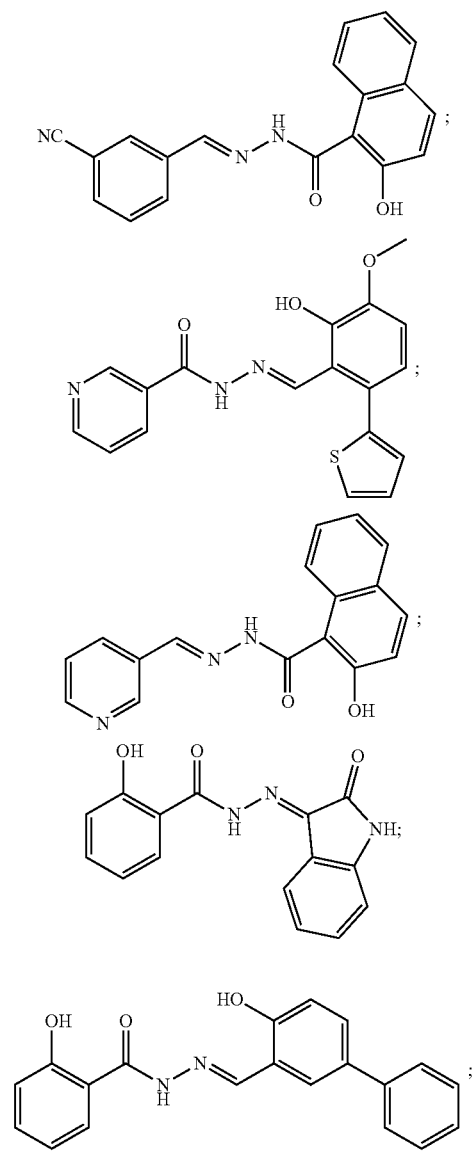

-continued

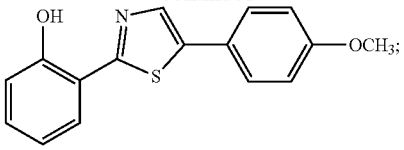

pharmaceutically acceptable salts, tautomers, and solvates thereof.

In some embodiments, the RRmod can include a compound having the structure of formula (III):

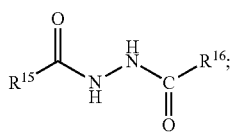

(III)

or a pharmaceutically acceptable salt, tautomer, or solvate thereof, wherein:

$R^{15}$ and $R^{16}$ are independently selected from the group consisting of substituted or unsubstituted aryl, a substituted or unsubstituted heteroaryl, a substituted or unsubstituted cycloalkyl, and a substituted or unsubstituted heterocyclyl.

In some embodiments, $R^{15}$ and $R^{16}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof.

In other embodiments, $R^{15}$ and $R^{16}$ are independently selected from the group consisting of:

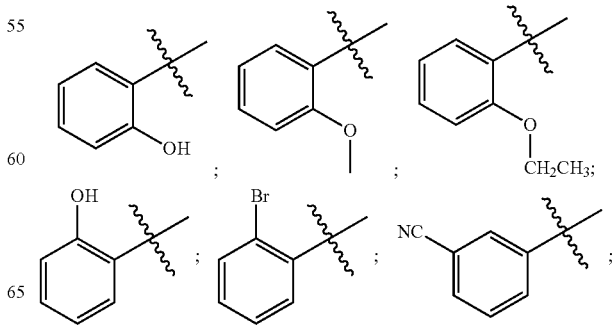

-continued

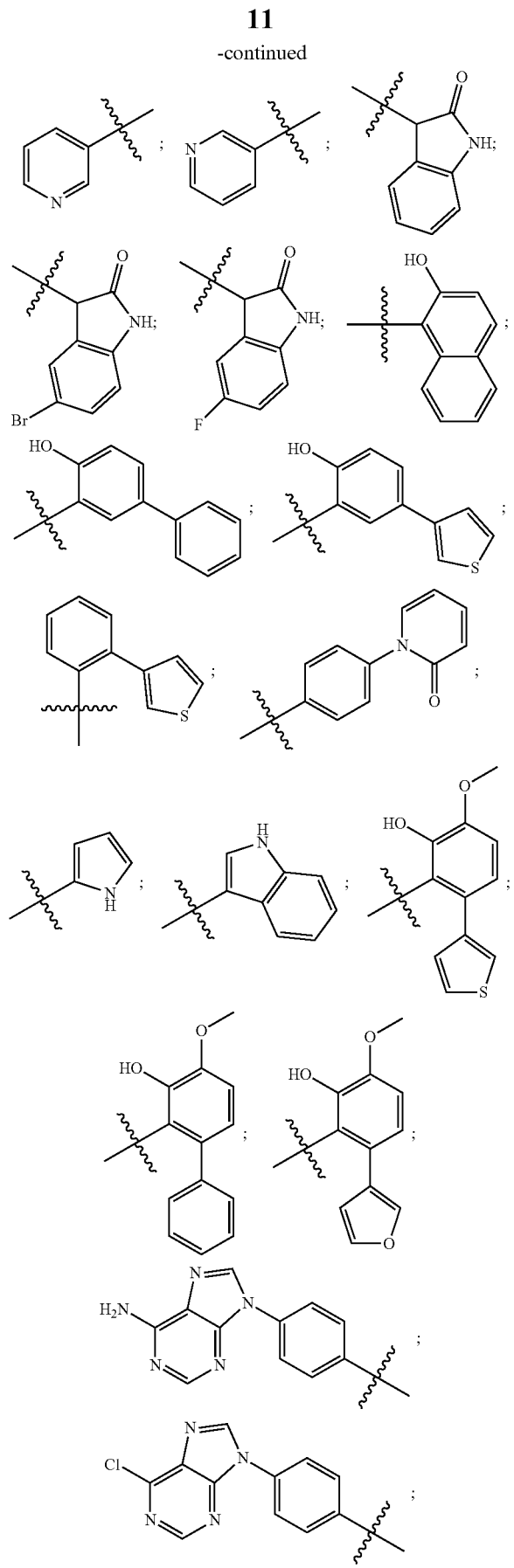

-continued

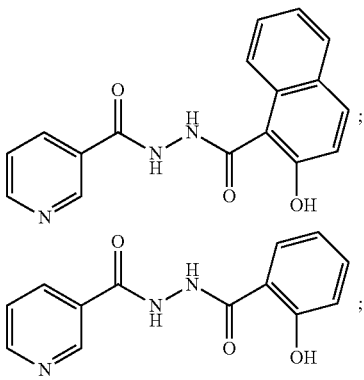

In certain embodiments, the compound having the structure of formula (III) can be selected from the group consisting of:

and pharmaceutically acceptable salts, tautomers, and solvatest thereof.

Other embodiments relate to a method of treating a neoplastic disorder. The method includes administering to neoplastic cells of the subject a therapeutically effective amount of a pharmaceutical composition. The pharmaceutical composition includes an RRmod. In some embodiments, the RRmod can include a compound having the structure of formula I, II, or III. The therapeutically effective amount of an RRmod is an amount effective to inhibit neoplastic cell growth in the subject.

Still other embodiments relate to a pharmaceutical composition that includes an RRmod. The RRmod inhibits cell growth when administered to a neoplastic cell. In some embodiments, the RRmod can include a compound having the structure of formula I, II, or III.

DETAILED DESCRIPTION

Figure 1:
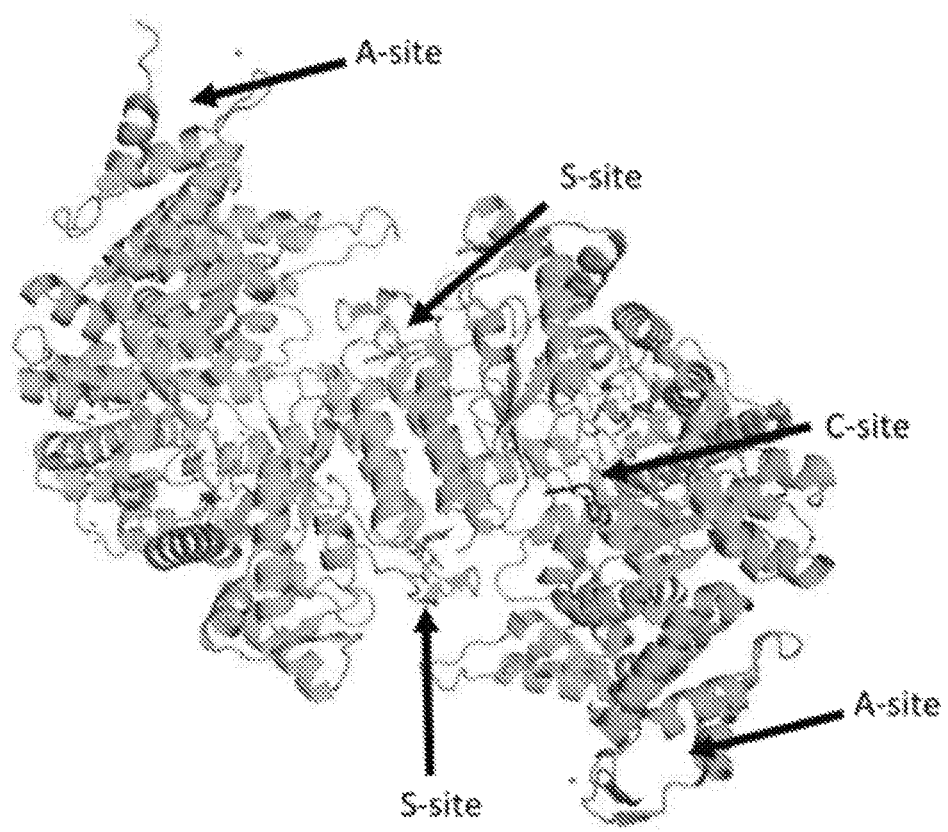
FIG. 1 illustrates the structure of hRRM1 dimer.
Figure 2A:
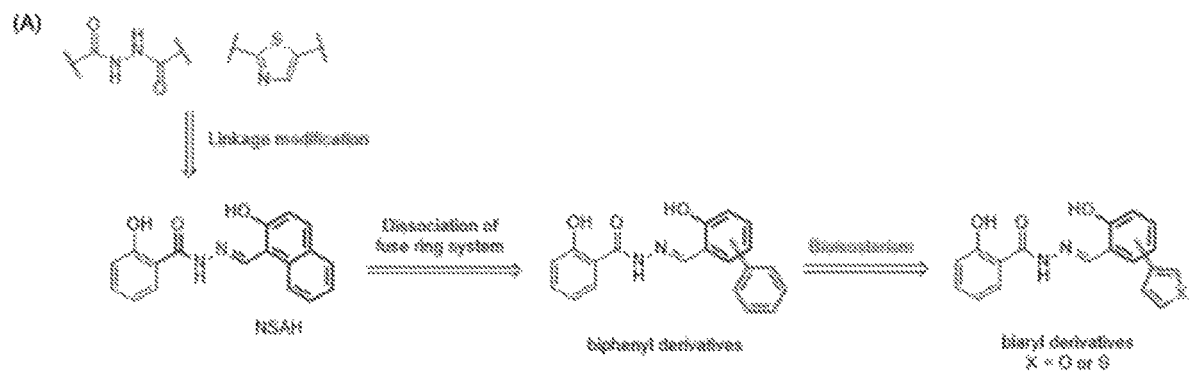
FIGS. 2(A-B) are a schematic and structures illustration of synthesized compounds.
Figure 2B:
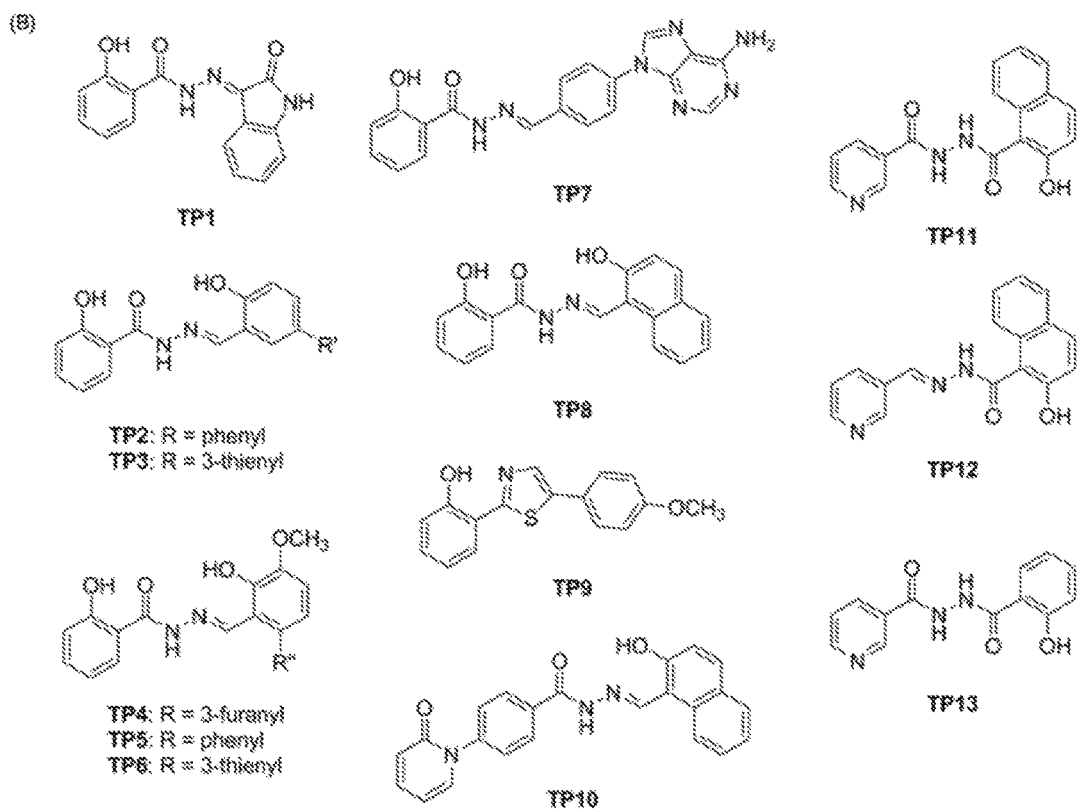

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods. The term "pharmaceutically acceptable salts" also includes those obtained by reacting the active compound functioning as an acid, with an inorganic or organic base to form a salt, for example salts of ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, and the like. Non limiting examples of inorganic or metal salts include lithium, sodium, calcium, potassium, magnesium salts and the like.

Additionally, the salts of the compounds described herein, can exist in either hydrated or unhydrated (the anhydrous) form or as solvates with other solvent molecules. on-limiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds and salts described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The terms below, as used herein, have the following meanings, unless indicated otherwise:

"Amino" refers to the —$NH_2$ radical.
"Cyano" refers to the —CN radical.
"Halo" or "halogen" refers to bromo, chloro, fluoro or iodo radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.
"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —$C(=O)R_a$ moiety, wherein R a is an alkyl, alkenyl or alkynyl radical as defined above. A non-limiting example of an alkyl carbonyl is the methyl carbonyl ("acetal") moiety. Alkylcarbonyl groups can also be referred to as "$C_w$-$C_z$ acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_2$-$C_{10}$ alkenyl, or $C_2$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from phenyl (benzene), aceanthrylene, acenaphthylene, acephenanthrylene, anthracene, azulene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —$R_b$—$R_c$ where $R_b$ is an alkylene group as defined above and $R_c$ is one or more aryl radicals as defined above. Aralkyl radicals include, but are not limited to, benzyl, diphenylmethyl and the like. Unless stated otherwise specifically in the specification, an aralkyl group can be optionally substituted.

"Aralkenyl" or "arylalkenyl" refers to a radical of the formula —$R_b$—$R_c$ where $R_b$ is an alkenylene group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$—$R_c$ where $R_b$ is an alkynylene group as defined above and $R_c$ is one or more aryl radicals as defined above. Unless stated otherwise specifically in the specification, an aralkynyl group can be optionally substituted.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl. Cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused, bridged, or spiral ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused, bridged, or spiral ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused, bridged, or spiral ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkynyl group can be optionally substituted.

"Heterocyclyl," "heterocyclic ring" or "heterocycle" refers to a stable 3- to 20-membered non-aromatic, partially aromatic, or aromatic ring radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused, bridged, and spiral ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, aziridinyl, oextanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, pyridine-one, and the like. The point of attachment of the heterocyclyl, heterocyclic ring, or heterocycle to the rest of the molecule by a single bond is through a ring member atom, which can be carbon or nitrogen. Unless stated otherwise specifically in the specification, a heterocyclyl group can be optionally substituted.

"Heterocyclylalkyl" refers to a radical of the formula —$R_b$—$R_e$ where $R_b$ is an alkylene group as defined above and $R_e$ is a heterocyclyl radical as defined above. Unless stated otherwise specifically in the specification, a heterocyclylalkyl group can be optionally substituted.

"Heterocyclylalkenyl" refers to a radical of the formula —$R_b$—$R_e$ where $R_b$ is an alkenylene group as defined above and $R_e$ is a heterocyclyl radical as defined above. Unless stated otherwise specifically in the specification, a heterocyclylalkenyl group can be optionally substituted.

"Heterocyclylalkynyl" refers to a radical of the formula —$R_b$—$R_e$ where $R_b$ is an alkynylene group as defined above and $R_e$ is a heterocyclyl radical as defined above. Unless stated otherwise specifically in the specification, a heterocyclylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical one to thirteen carbon atoms and one to six heteroatoms selected from the group consisting of nitrogen, oxygen and sulfur, as the ring member. For purposes of this invention, the heteroaryl radical can be a monocyclic, bicyclic, tricyclic or tetracyclic ring system, which can include fused or bridged ring systems, wherein at least one ring containing a heteroatom ring member is aromatic. The nitrogen, carbon or sulfur atoms in the heteroaryl radical can be optionally oxidized and the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrazolopyridine, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula —$R_b$—$R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula —$R_b$—$R_f$ where $R_b$ is an alkynylene chain as defined above and $R_f$ is a heteroaryl radical as defined above. Unless stated otherwise specifically in the specification, a heteroarylalkynyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (e.g., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl, heteroarylalkyl, heteroarylalkenyl, heteroarylalkynyl, etc) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol "

" (hereinafter can be referred to as "a point of attachment bond") denotes a bond that is a point of attachment between two chemical entities, one of which is depicted as being attached to the point of attachment bond and the other of which is not depicted as being attached to the point of attachment bond. For example, "

" indicates that the chemical entity "A" is bonded to another chemical entity via the point of attachment bond. Furthermore, the specific point of attachment to the non-depicted chemical entity can be specified by inference. For example, the compound

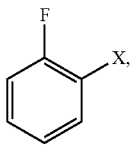

wherein X is "

" infers that the point of attachment bond is the bond by which X is depicted as being attached to the phenyl ring at the ortho position relative to fluorine.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

The term "neoplasm" refers to any abnormal mass of cells or tissue as a result of neoplasia. The neoplasm may be benign, potentially malignant (precancerous), or malignant (cancerous). An adenoma is an example of a neoplasm.

The terms "adenoma", "colon adenoma" and "polyp" are used herein to describe any precancerous neoplasm of the colon.

The term "colon" as used herein is intended to encompass the right colon (including the cecum), the transverse colon, the left colon and the rectum.

The terms "colorectal cancer" and "colon cancer" are used interchangeably herein to refer to any cancerous neoplasia of the colon (including the rectum, as defined above).

The term "anticancer agent" refers to a compound which treats a cancer (e.g., a compound which is useful in the treatment of a cancer). The anticancer effect(s) may arise through one or more mechanisms including, but not limited to, the regulation of cell proliferation, the inhibition of cell cycle progression, the inhibition of cell growth, the inhibition of angiogenesis, the inhibition of metastasis, the inhibition of invasion (e.g., the spread of tumor cells into healthy neighboring tissue), or the promotion of apoptosis. The term "antineoplastic" is used herein to mean a chemotherapeutic intended to inhibit or prevent the maturation and proliferation of neoplasms, by targeting the DNA.

The term "cell growth" is used in the contexts of cell development and cell division (reproduction). When used in the context of cell division, it refers to growth of cell populations, where one cell (the "mother cell") grows and divides to produce two "daughter cells" (M phase). When used in the context of cell development, the term refers to increase in cytoplasmic and organelle volume (G1 phase), as well as increase in genetic material before replication (G2 phase).

The terms "neoplastic cell", "cancer cell" or "tumor cell" refer to cells that divide at an abnormal (i.e., increased) rate.

A neoplastic cell or neoplasm (tumor) can be benign, potentially malignant, or malignant. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

The term "epitope" refers to a physical structure on a molecule that interacts with a selective component, e.g., the selective component such as an RRmod described herein. In exemplary embodiments, epitope refers to a desired region on a target molecule that specifically interacts with a selectivity component.

Embodiments described herein relate to ribonucleotide reductase modulators (RRmods), pharmaceutical compositions comprising RRmods, therapeutic uses of RRmods, as well as compounds found to be specifically effective as allosteric modulators of ribonucleotide reductase activity in neoplastic cells.

Ribonucleotide reductase enzyme activity is required for de novo DNA synthesis by catalyzing ribonucleotides to deoxy ribonucleotides and maintaining a balanced nucleotide precursor molecule pool. Since the proliferation of cancer cells requires excess dNTPs for DNA synthesis, it is believed that RRmods that specifically target RR1 can be employed to inhibit cell growth and proliferation of neoplastic cells through the modulation of ribonucleotide reductase enzyme activity.

It was found that the large subunit ($\alpha$-subunit or hRRM1) of ribonuecleotide reductase (RR) includes four potentially druggable sites (see FIG. 1A). These sites include the A (activity)-site, the S (specificity)-site, the C (catalytic)-site and the P (peptide)-site. Using X-ray crystallography, an additional epitope of hRRM1, the M-site, was found to be in the hexamer interface of hRRM1. The M-site is a surface pocket including residues constituting the ($\beta$-cap located on one dimer and the loop involving residue 480 belonging to an adjacent dimer at the hexamer interface.

It was found that the M-site can be targeted by small molecules to modulate ribonucleotide reductase activity. Using in silico high throughput screening and RR activity and growth inhibition cell culture in vitro assays, small molecules that bind to or complex with M-site or the catalytic C-site of hRRM1 were identified that were capable of allosterically inhibiting or activating the enzyme. These identified small molecules and analogs thereof can be used in a method of modulating ribonucleotide reductase activity in a neoplastic cell to inhibit neoplastic cell growth.

In some embodiments, RRmods described herein include agents capable of binding to or complexing with an epitope of hRRM1. In some embodiments the RRmod binds to the hexamer interface M-site or the catalytic C-site of hRRM1, and allosterically modulates ribonucleotide reductase enzyme activity, thereby affecting de novo DNA synthesis, cell growth and proliferation of neoplastic cells.

In certain embodiments, the RRmod is a small molecule. Exemplary data of small molecule compounds found to be specifically effective as allosteric modulators of ribonucleotide reductase activity are provided in the Example below. In particular, the disclosed compounds had activity in inhibiting the ribonucleotide reductase activity in DNA synthesis assays and for killing carcinomas in a cell-based assay, generally with a micromolar $IC_{50}$.

In some embodiments, the RRmod can include a compound having the structure of formula (I):

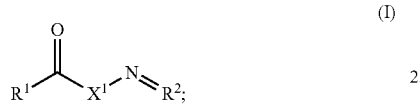

(I)

or a pharmaceutically acceptable salt, tautomer, or solvate thereof, wherein: $X^1$ is NH or 0;
$R^1$ and $R^2$ are independently selected from the group consisting of substituted or unsubstituted aryl, a substituted or unsubstituted heteroaryl, a substituted or unsubstituted cycloalkyl, and a substituted or unsubstituted heterocyclyl.

In some embodiments, $R^2$ is not a hydroxynaphthalenyl or an indole.

In some embodiments, $R^1$ is selected from the group consisting of:

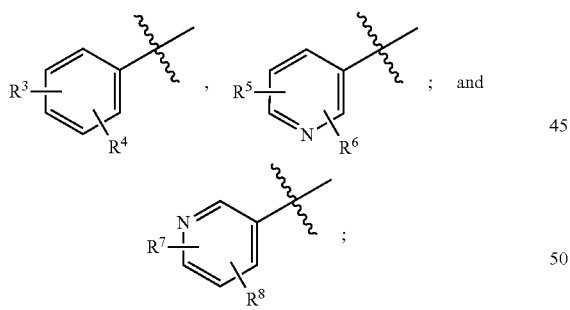

wherein each of $R^3$, $R^4$, $R^5$, $R^6$, $R^7$, and $R^8$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl) 3, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, and combinations thereof.

In other embodiments, $R^1$ is selected from the group consisting of:

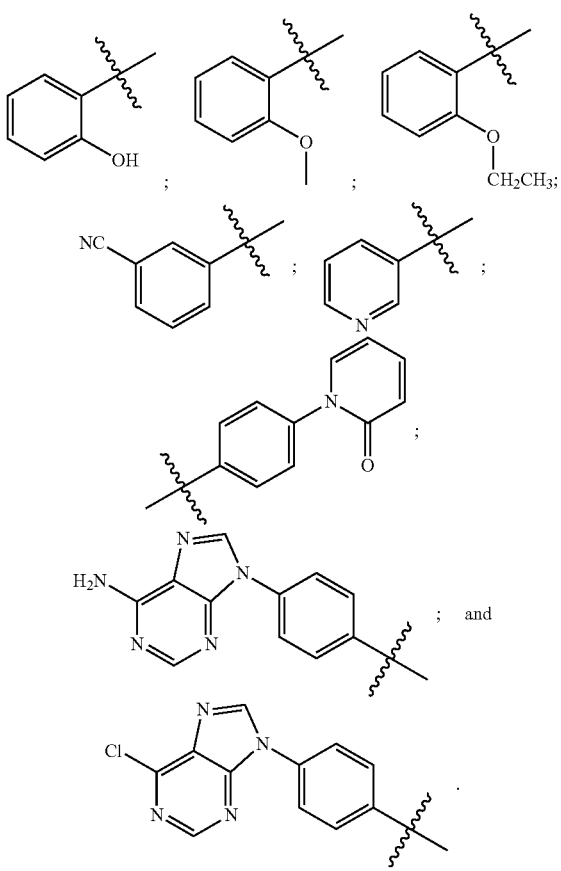

In still other embodiments, $R^1$ has the structure of:

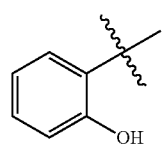

In some embodiments. $R^2$ is selected from the grotto consisting of:

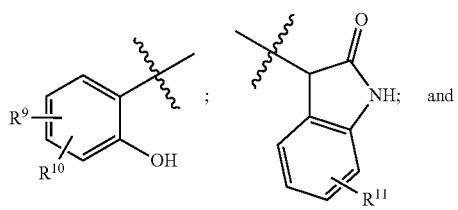

-continued

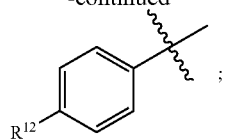

wherein each of $R^9$, $R^{10}$, $R^{11}$ and $R^{12}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, and combinations thereof.

In some embodiments, $R^2$ is selected from the group consisting of:

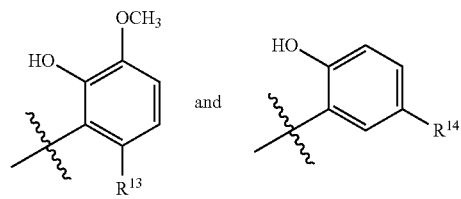

wherein $R^{13}$ and $R^{14}$ are each independently selected from the group consisting of substituted or unsubstituted aryl, a substituted or unsubstituted heteroaryl, a substituted or unsubstituted cycloalkyl, and a substituted or unsubstituted heterocyclyl. For example, $R^{13}$ and $R^{14}$ can each independently be a substituted or unsubstituted furanyl, phenyl, or thienyl.

In some embodiments, $R^2$ is selected from the group consisting of:

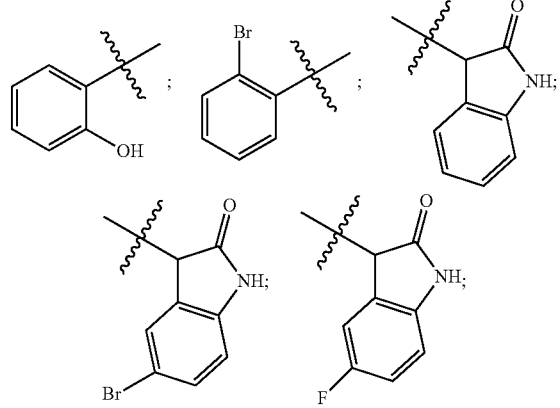

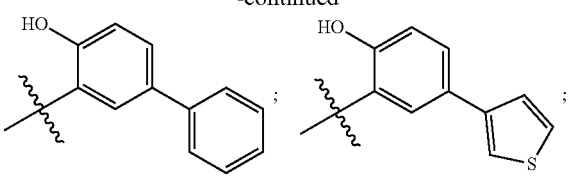

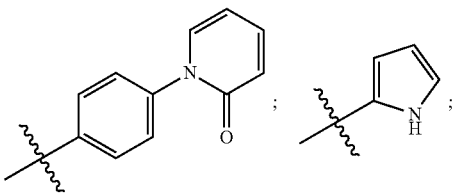

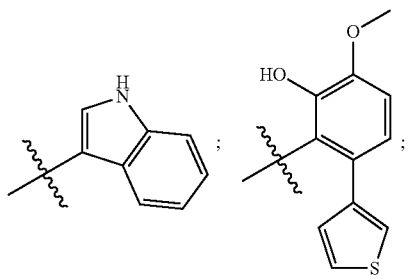

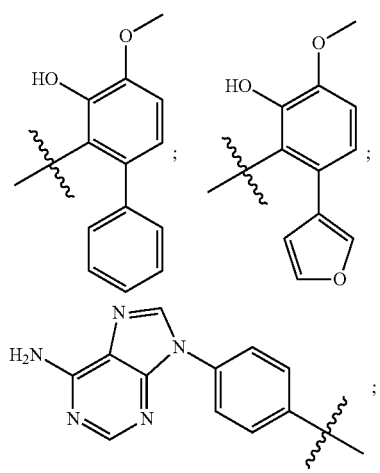

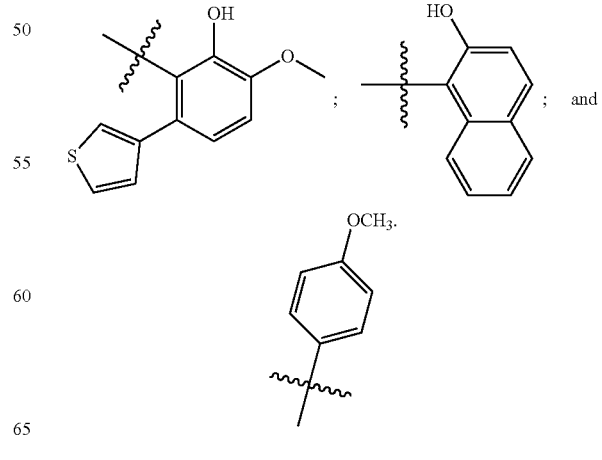

In some embodiments, the RRmod can include a compound having the formula (II):

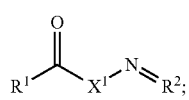
(II)

or a pharmaceutically acceptable salt, tautomer, or solvate thereof, wherein: $X^1$ is NH or O;

$R^1$ is selected from the group consisting of:

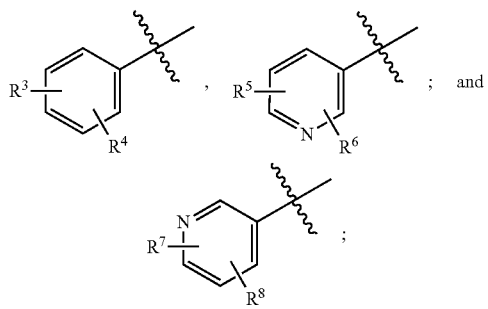

$R^2$ is selected from the group consisting of:

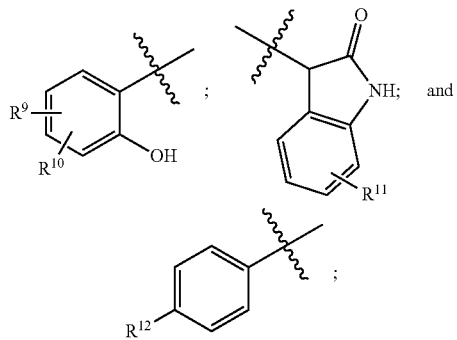

each of $R^3$, $R^4$, $R^5$, $R^6$, $R^7$, $R^8$, $R^9$, $R^{10}$, $R^{11}$, and $R^{12}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl) 3, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{26}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{26}$ arylsulfinyl, $C_1$-$C_{24}$ alkylsulfonyl, $C_5$-$C_{26}$ arylsulfonyl, sulfonamide, phosphono, phosphonato, phosphinato, phospho, phosphino, polyalkylethers, phosphates, phosphate esters, and combinations thereof.

In some embodiments, $R^2$ is selected from the group consisting of:

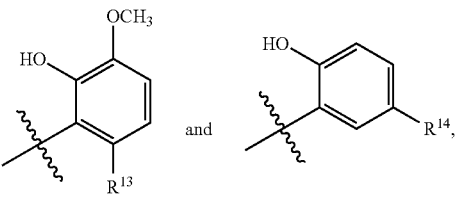

wherein $R^{13}$ and $R^{14}$ are each independently selected from the group consisting of substituted or unsubstituted aryl, a substituted or unsubstituted heteroaryl, a substituted or unsubstituted cycloalkyl, and a substituted or unsubstituted heterocyclyl. For example, $R^{13}$ and $R^{14}$ can each independently be a substituted or unsubstituted furanyl, phenyl, or thienyl.

In certain embodiments, an RRmod having the structure of formula (I) or formula (II) can be selected from the group consisting of:

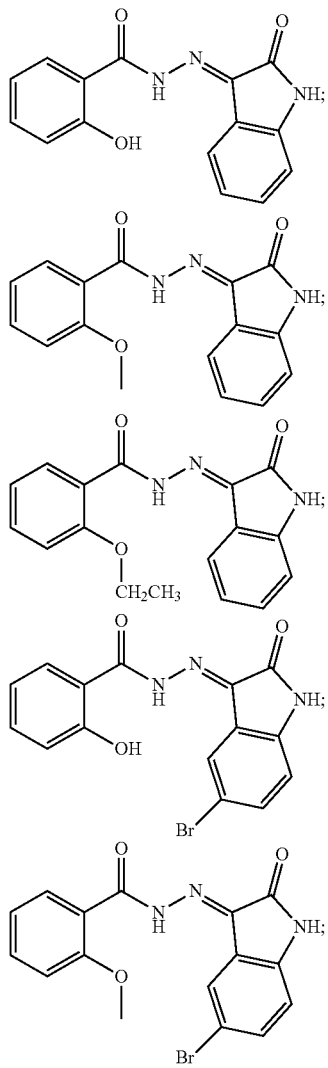

-continued
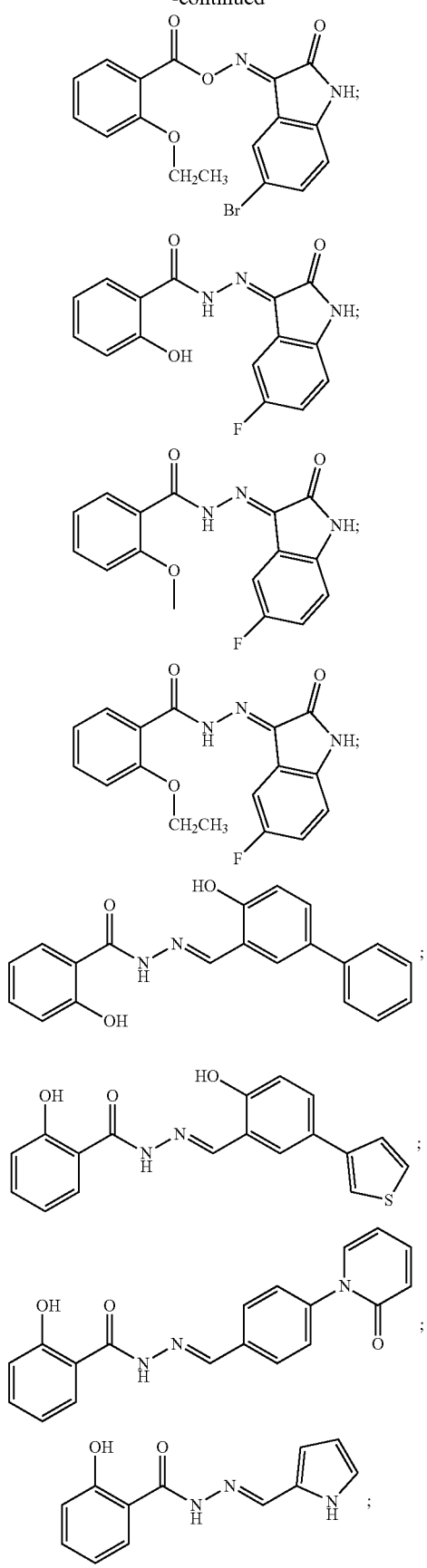
-continued
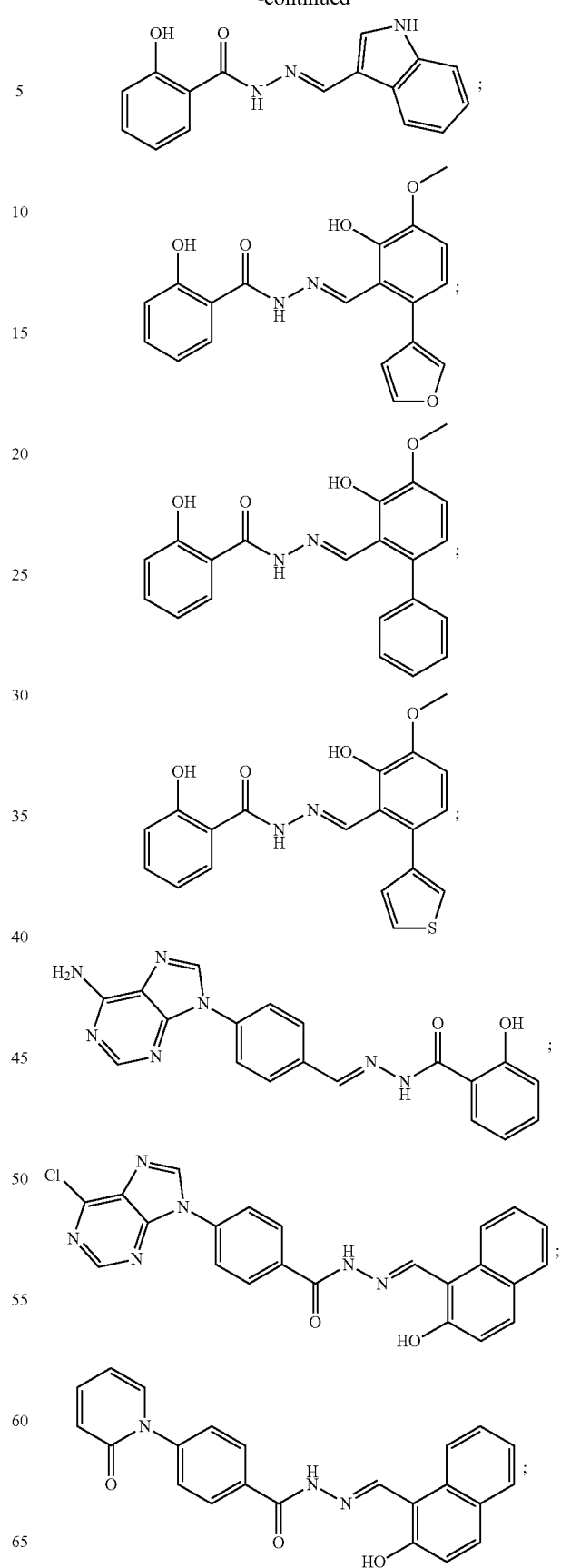

-continued

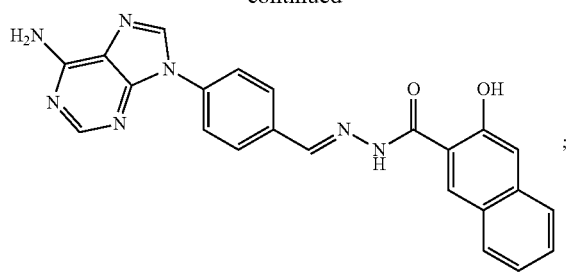

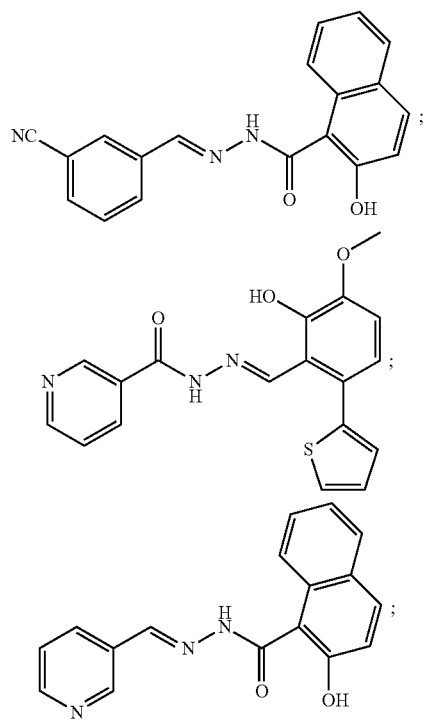

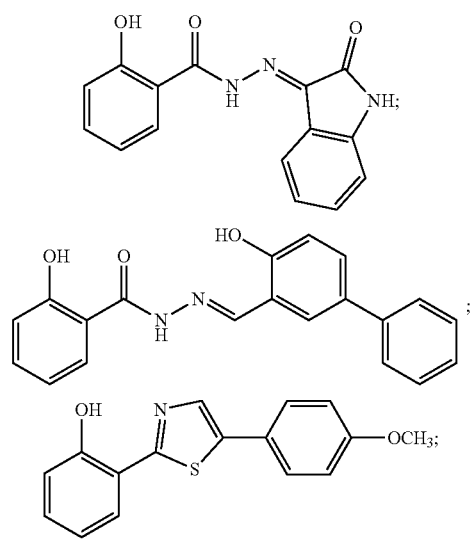

pharmaceutically acceptable salts, tautomers, and solvates thereof.

In some embodiments, the RRmod can include a compound having the structure of formula (III):

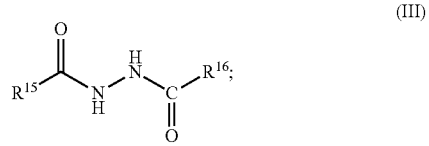

(III)

or a pharmaceutically acceptable salt, tautomer, or solvate thereof, wherein:
$R^{15}$ and $R^{16}$ are independently selected from the group consisting of substituted or unsubstituted aryl, a substituted or unsubstituted heteroaryl, a substituted or unsubstituted cycloalkyl, and a substituted or unsubstituted heterocyclyl.

In some embodiments, $R^{15}$ and $R^{16}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof.

In other embodiments, $R^{15}$ and $R^{16}$ are independently selected from the group consisting of:

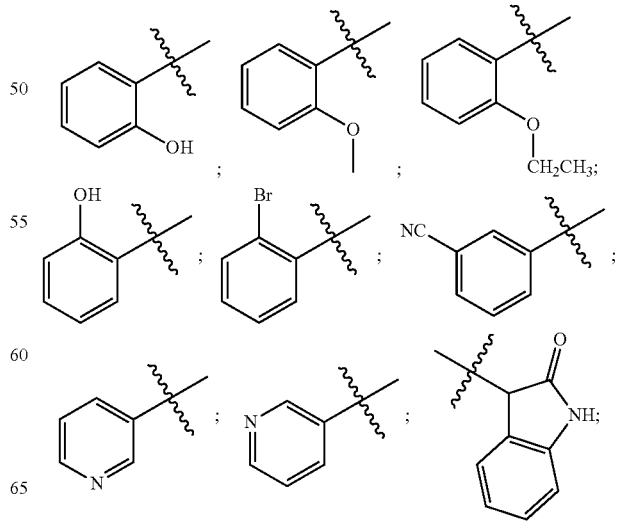

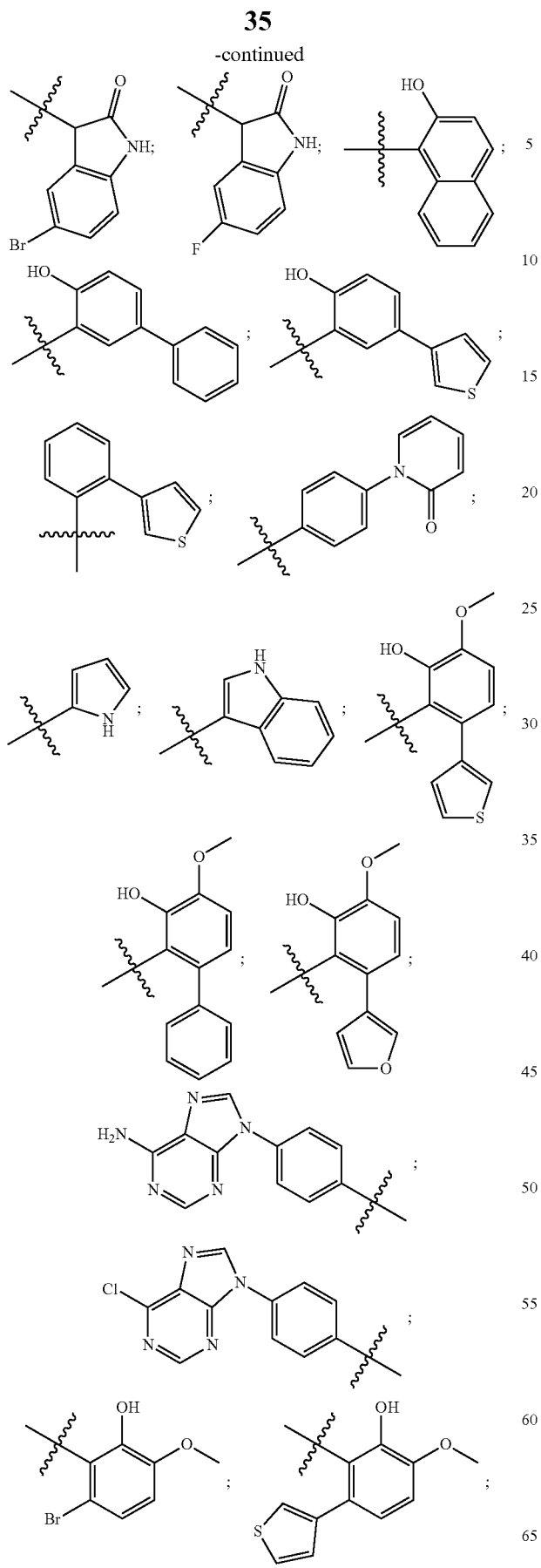

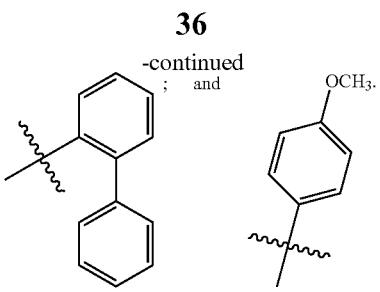

In certain embodiments, the compound having the structure of formula (III) can be selected from the group consisting of:

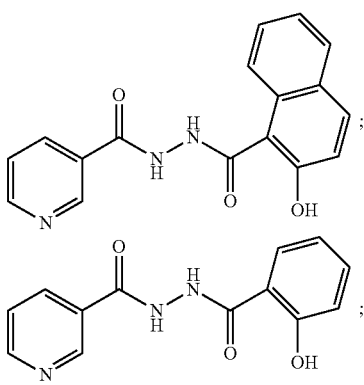

and pharmaceutically acceptable salts, tautomers, and solavates thereof.

Additional RRmods can be identified by screening compounds for the ability to modulate (e.g., inhibit or activate) ribonucleotide reductase enzyme activity. Candidate RRmods can be screened for function by a variety of techniques known in the art and/or disclosed within the instant application. Candidate compounds may be screened individually, in combination, or as a library of compounds.

Candidate compounds screened include chemical compounds. In some aspects, the candidate compound is a small organic molecule having a molecular weight of more than about 50 and less than about 2,500 daltons. Compounds screened are also found among biomolecules including, but not limited to: peptides, saccharides, fatty acids, steroids, pheromones, purines, pyrimidines, derivatives, structural analogs or combinations thereof. The compounds screened can include functional groups necessary for structural interaction with proteins, particularly hydrogen bonding, and typically include at least an amine, carbonyl, hydroxyl, or carboxyl group.

Candidate compounds can be obtained from a wide variety of sources including libraries of synthetic or natural compounds. Compounds to be screened can be produced, for example, by bacteria, yeast or other organisms (e.g., natural products), produced chemically (e.g., small molecules, including peptidomimetics), or produced recombinantly. It is further contemplated that natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In many drug screening programs, with test libraries of compounds and natural extracts, high throughput assays are desirable in order to maximize the number of compounds surveyed in a given period of time. Assays described herein may be developed with purified or semi-purified proteins or with lysates. These assays are often preferred as "primary" screens in that they can be generated to permit rapid development and relatively easy detection of an alteration in a molecular target, which is mediated by a test agent. Assays described herein can include cell-based assays. Cell-based assays may be performed as either a primary screen, or as a secondary screen to confirm the activity of compounds identified in a cell free screen, such as an in silico screen.

Embodiments described herein also relate to a method of screening in silico for a compound effective as an RRmod. For example, a 3-D model of the hexamer interface epitope of RR1 targeted by small molecules can be used to provide a pharmacophore using X-ray Crystallography. An initial model can then be generated using a suitable protein modeling software program. In some aspects, the model can then be subjected to energy refinement with a software program such as SURFLEX dock. The pharmacophore can be modified to comply to the Lipinski limits to design drug-like molecules with good bioavailability. In one embodiment, the template used for docking was the hexamer interface of ribonucleotide reductase as shown in FIG. 1.

Once a model is built, small molecule RRmods that bind to ribonucleotide reductase at the hexamer interface of RR1 can be identified by methods well known in the relevant art using in silico conformation screening techniques. For example, virtual screening of the University of Cincinnati Drug Discovery Center (UC DCC) Library of 350,000 compounds can be performed using the drug discovery software SYBYLX1.3 (Tripos, St. Louis, MO). Such software can also be used to design modified analogs of compounds for use as RRmods. In parallel, ZINC and other commercial databases can be searched using within SYBYLX1.3 software for lead compounds that satisfy the pharmacophore. These hits can be docked and scored using SURFLEX dock option in SYBYLX1.3. The best hits can then be discriminated using two scoring functions called, a docking score and the C-score. The docking score is theoretically equivalent to the negative logarithm of $K_a$, while C-score is a consensus scoring function. Hence, docking scores that are equal to 6 would mean a theoretical $K_a$ of micromolar. The maximum C-score that can be obtained is five. Based on these criteria, after virtually screening the library, the best scoring candidates can be selected and then tested using various in vitro and cell based assays described herein and known in the art for efficacy. The larger numbers obtained for dock score and C-scores greater than 6 and 4-5 respectively represents the high ranking inhibitors that are predicted to have high affinities.

In some aspects, about 20,000 compounds can be selected from in silico screening for an in vitro high-throughput screening (HTS). HTS can be carried out using an automated HTS system which performs biochemical and cell-based assays using 96 or 384-well microtiter plates. The system includes detectors, $CO_2$ incubators, pipetting systems, a plate washer, centrifuge, a storage unit, bar code readers, xyz robots, turntables, and pushers necessary for fully automated screening. A Jobin Yvon-Spex fluorescence spectrophotometer can be used to record the spectra. Alternatively, a multimode PERKIN-ELMER plate reader can be used for detecting fluorescence intensity, fluorescence polarization, fluorescence resonance energy transfer, luminescence, or absorbance using ZEISS optics and a sensitive CCD camera. The PERKIN-ELMER Opera detector performs high content screening using confocal microscopy and image analysis software powered by onboard servers. Lasers and CCD cameras allow measurement of subcellular localization, binding events or any other microscopic images which can be rapidly quantitated. Image analysis is performed immediately after the image is captured and stored in a database. All other data can be analyzed using GENEDATA HTS analysis software (Switzerland), stored in a GENEDATA database based on ORACLE.

In some embodiments, in vitro HTS includes a fluorescence based assay adapted for HTS. For example, in vitro HTS can employ tryptophan fluorescence quenching. The binding sites of proteins are known to often contain tryptophan (Trp) residues, whose fluorescent properties may be altered upon ligand binding. Conformational changes within the binding site or simply the presence of the ligand can result in either fluorescence quenching or enhancement, which may be utilized to quantitatively investigate protein-ligand interactions. Change in intrinsic tryptophan fluorescence is used to measure the binding of a candidate agent to a targeted binding site of ribonucleotide reductase. The trytophan fluorescence spectra of Hurl (Human ribonucleotide reductase) and a candidate compound can be recorded and then compared in order to determine the extent of quenching. The ribonucleotide reductase samples can be titrated with 65 μM candidate compounds at room temperature where a decrease in fluorescence, or quenching, can be correlated with the binding affinity of the candidate compound to the targeted binding site of ribonucleotide reductase and/or a conformational change in the targeted ribonucleotide reductase binding site.

In some aspects, candidate RRmod compounds, including those collected from an in silico similarity search or HTS assay, may be further screened for efficacy using in vitro and/or in vivo experimental screening methods known in the art. The efficacy of an identified compound can be assessed by generating dose response curves from data obtained using various concentrations of the test compound. Moreover, a control assay can also be performed to provide a baseline for comparison. Such candidates can be further tested for their effects on cancer and tumor cell growth, proliferation, apoptosis, differentiation, and transformation compared to controls as well as their ability to: inhibit de novo DNA synthesis in vitro; unbalance nucleotide pool of DNA precursor molecules in vitro; modulate ribonucleotide reductase activity in vitro; and/or for other properties, such as the ability to inhibit cell growth and increase the toxicity of neoplastic cells in vivo.

In some embodiments, assays used for in vitro screening of candidate compounds for cell growth inhibition can include DNA synthesis assays and MTT colorimetric assays to measure cell metabolism. For example, a DNA synthesis assay can include the steps of: (a) contacting the neoplastic cell with various concentrations of a candidate compound; and (b) comparing the DNA synthesis of the cell in step (a) with the DNA synthesis of the cell in the absence of the compound so as to determine whether the compound significantly inhibits ribonucleotide reductase activity, thereby reducing the growth of the cell. One can also determine the $IC_{50}$ of a candidate compound if the compound is found to significantly inhibit ribonucleotide reductase activity. The $IC_{50}$ of a drug can be determined by constructing a dose-response curve and examining the effect of different concentrations of a candidate agent on cell growth and/or ribonucleotide reductase enzyme activity. $IC_{50}$ values can be calculated for a given compound by determining the concentration needed to inhibit half of the maximum biological response of the compound.

For in vivo screening of candidate compounds, the candidate compound can be administered in any manner desired and/or appropriate for delivery of the compound in order to affect a desired result. For example, the candidate compound can be administered to a mammalian subject by injection (e.g., by injection intravenously, intramuscularly, subcutaneously, or directly into the tissue in which the desired affect is to be achieved), topically, orally, or by any other desirable means.

Normally, this screen will involve a number of animals receiving varying amounts and concentrations of the candidate compounds (from no compound to an amount of compound that approaches an upper limit of the amount that can be delivered successfully to the animal), and may include delivery of the compound in different formulations. The compounds can be administered singly or can be combined in combinations of two or more, especially where administration of a combination of compounds may result in a synergistic effect.

The effect of compound administration upon the animal model can be monitored by any suitable method such as assessing the number and size of tumors, overall health, survival rate, etc. A candidate compound is identified as an effective compound for use in the treatment of a neoplastic disorder in a subject where candidate compound inhibits neoplastic cell growth in the animal in a desirable manner (e.g., by binding to the Sm11 allosteric binding site of ribonucleotide reductase and allosterically inhibiting the enzyme's activity, etc.). In some aspects, effective compounds can be identified as having low toxicity in vivo.

As shown in the Example below, RRmods disclosed herein have been shown to bind to epitopes (e.g., M-site or C-site) of the large α-subunit of RR1 and inhibit growth of multiple cancer cell types in vitro, supporting the use of these RRmods to treat a wide range of neoplastic diseases and disorders. Thus, in accordance with another embodiment, RRmods described herein can be used for the preparation of a pharmaceutical composition for the treatment of a neoplastic disorder in a subject. In one embodiment, the subject is suffering from a neoplastic disorder characterized by increased cell growth. In another embodiment, the subject is suffering from cancer.

A therapeutically effective amount of an RRmod described herein can be administered to a subject for the treatment of a variety of conditions in order to inhibit cell growth in the subject. Such conditions include, without being limited thereto, neoplastic disorder, and in particular all types of solid tumors; skin proliferative diseases (e.g., psoriasis); and a variety of benign hyperplasic disorders.

In one aspect, the neoplastic disorder is cancer. The cancer can include, but is not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma. In certain aspects, the cancer is a pancreatic, breast, lung, colon or glyoblastoma cancer.

In another aspect, the neoplastic disorder is a solid tumor. Exemplary solid tumors include carcinomas, sarcomas, adenomas, and cancers of neuronal origin and if fact to any type of cancer which does not originate from the hematopoeitic cells and in particular concerns: carcinoma, sarcoma, adenoma, hepatocellular carcinoma, hepatocellularcarcinoma, hepatoblastoma, rhabdomyosarcoma, esophageal carcinoma, thyroid carcinoma, ganglioblastoma, fibrosarcoma, myxosarcoma, liposarcoma, cohndrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small lung carcinoma, bladder carcinoma, epithelial carcinoma, glioma, astrocyoma, medulloblastoma, craniopharyngioma, ependynoma, pinealoma, retinoblastoma, multiple myeloma, rectal carcinoma, thyroid cancer, head and neck cancer, brain cancer, cancer of the peripheral nervous system, cancer of the central nervous system, neuroblastoma, cancer of the endometrium, as well as metastasis of all the above.

Benign hyperplasic disorders include, without being limited thereto, benign prostate hyperplasia (BPH), non-tumorigenic polyps in the digestive tract, in the uterus and others.

In addition to cancer, the RRmods disclosed herein may be used to treat other conditions associated with aberrant ribonucleotide reductase enzyme activity such as for example various mitochondrial, redox-related, degenerative diseases, and viruses such as HIV.

When used as therapeutic agents in the treatment of neoplastic disorders, the RRmods can be conveniently formulated into pharmaceutical formulations composed of one or more of the compounds (e.g., RRmods of formulas (I-II) or an RRmod identified by a screening assay as described above) in association with a pharmaceutically acceptable carrier or excipient. (See Remington: The Science and Practice of Pharmacy (Gennaro ed. 22nd Edition, Pharmaceutical Press, London, U K, 2012), which discloses typical carriers and conventional methods of preparing pharmaceutical formulations).

In making the compositions, the RRmod is usually mixed with the excipient, diluted by an excipient or enclosed within a carrier which can be in the form of a capsule, sachet, paper or other container. When the excipient serves as a diluent, it can be a solid, semi-solid, or liquid material, which acts as a vehicle, carrier or medium for the RRmod. Thus, the compositions can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders. The RRmods can also be administered to a subject as a stabilized prodrug to increase the activity, bioavailability, stability or otherwise alter the properties of the RRmod.

The effective amount of RRmod in the pharmaceutical composition and unit dosage form thereof may be varied or adjusted widely depending upon the particular application, the manner or introduction, the potency of the particular compound, and the desired concentration.

The effective amount is typically determined in appropriately designed clinical trials (dose range studies) and the person versed in the art will know how to properly conduct such trials in order to determine the effective amount. As generally known, an effective amount depends on a variety of factors including the affinity of the RRmod to the targeting binding site (e.g., the M-site or C-site of hRRM1), its distribution profile within the body, a variety of pharmacological parameters such as half life in the body, on undesired side effects, if any, on factors such as age and gender, etc.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In this case, the composition will typically be administered over an extended period of time in a single daily dose, in several doses a day, as a single dose and in several days, etc. The treatment period will generally have a length proportional to the length of the disease process and the specific RRmod effectiveness and the patient species being treated.

RRmods and pharmaceutical compositions thereof can be administered to the subject by any suitable means, including, for example, oral, intravenous, intramuscular, intra-arterial, subcutaneous, intranasal, via the lungs (inhalation) and through local administration.

RRmods described herein can be used as single agents or in combination or in conjunction with one or more other therapeutic agents in the treatment of the aforementioned diseases, disorders and conditions for which RRmods or the other agents have utility. In some embodiments, a combination of an RRmod and other therapeutic agent together is safer or more effective than either drug alone.

In some embodiments, the other therapeutic agent used in a combination therapy can include at least one anti-proliferative agent selected from the group consisting at least one of a chemotherapeutic agent, an anticancer agent, an antimetabolite, a DNA damaging agent, an antitumorgenic agent, an antimitotic agent, an antiviral agent, an antineoplastic agent, an immunotherapeutic agent, and a radiotherapeutic agent. Additional therapeutic agents used in combination therapies with RRmods can include biguanides (e.g., metformin, phenformin and buformin), AP endonuclease inhibitors (e.g., methoxyamine (MX)), BER inhibitors including PARP inhibitors, and ribonucleotide reductase inhibiting agents. Exemplary ribonucleotide reductase inhibiting agents for use in conjunction with RRmods include $O^6$-methyl-arabinofuranosyl guanine (nelarabine), 2'-fluro-2'-deoxyarabinofuranosyl-2-chloroadenine (clofarabine), $N^4$-pentyloxycarbonyl-5'-deoxy-5-flurocytidine (capecitabine), 2,2-difluoro-2'-deoxyadenosine (cladribine), arabinofuranosyl-2-fluoroadenine (fludarabine), 2'-deoxycoformycin (pentostatin), 5-fluro-2'deoxyuridine, arabinofuranosylcytosine (cytarabine), 6-thioguanine, 5-fluorouracil, methotrexate, 6-mercaptopurine.

In some aspects, RRmods can be used in a combination therapy with an anti-proliferative agent. The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which can be included by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, anti-metastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids,selective inhibitors of proliferation and migration of endotheliai cells, selenium, stromelysin inhibitors, taxanes, vaccines, and *vinca* alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with an RRmod consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, gemcitabine, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the RRmods, consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastrointestinal mucosa, and fetal tissue. Examples of alkylating-type anti-proliferative agents that may be used include, but are not limited to, Shionogi 254-S, aldo-phosphamide analogs, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide (TMZ), teroxirone, tetraplatin and trimelamol.

A third family of anti-proliferative agents that may be used in combination therapy with the RRmods consists of antibiotic-type anti-proliferative agents. Examples of antibiotic-type anti-proliferative agents that may be used include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the RRmods consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety. Further 5-FU derivatives have been described in the following patents listed in JP 50-50383, JP 50-50384, JP 50-64281, JP 51-146482, and JP 53-84981 hereby individually incorporated by reference herein. Further synthetic nucleoside analogs include 4-amino-1-(2-deoxy-b-D-erythro-pentofuranosyl)-1,3,5-triazin-2(1H)-one (e.g., 5-aza-21-deoxycytidine, decitabine, or DACOGEN, Eisai Inc., Woodcliff Lake, N.J.). Other examples, of nucleoside analogs that can be used to treat cancer are listed in U.S. Pat. No. 4,000,137, which is incorporated herein by reference, Cytosine arabinoside (also referred to as Cytarabin, araC, and Cytosar) and 5-Azacytidine (VIDAZA, Celegene Corp., Summit, N.J.).

A fifth family of anti-proliferative agents that may be used in combination therapy with the RRmods consists of hormonal agents. Examples of hormonal-type anti-proliferative agents that may be used include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the RRmods consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW 502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI 941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K 477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY 186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N (retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org 10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In the instances of combination therapies described herein, it will be understood the administration further includes a pharmaceutically or therapeutically effective amount of the additional therapeutic agent in question. The second or additional therapeutic agents described herein may be administered in the doses and regimens known in the art or may be administered in low doses.

In some embodiments, the administration of a RRmod and an additional therapeutic agent can result in a synergistic effect. A "synergistic effect" as used herein means the combined effect of two or more therapeutic agents can be greater than the sum of the separate effects of the agents alone. For example, the combined effect of an RRmod, and an anticancer agent, such as metformin or another RRmod such as gemcitabine, can be greater than the sum of the separate effects of a single RRmod and metformin or gemcitabine alone.

In some embodiments, the combined effect of administering two or more RRmod compounds is greater than the sum of the separate effects of the RRmods alone. In certain embodiments, a NSAAH hydrazone RRmod, as described in PCT Patent Application PCT/US2016/065928, the subject matter of which is incorporated herein by reference in its entirety, can be administered in combination with one or more RRmods describe herein to produce a synergistic therapeutic effect. In a particular embodiment, a hydrazone RRmod described herein can be administered in combination with a second hydrazone (e.g., a NSAAH RRmod), oxidiazole, or thiazole RRmod to produce a synergistic therapeutic effect.

Where the combined effect of administering a RRmod and another therapeutic agent is greater than the sum of the separate effects of the RRmod and the other agent alone, the RRmod and/or therapeutic agent can be administered to the subject in a lower dose or even a sub-therapeutic dose. A benefit of lowering the dose of the combination therapeutic agents and therapies can include a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages.

The additional therapeutic agent can be administered by a route and in an amount commonly used therefore, contemporaneously or sequentially with a RRmod compound. When administered as a combination, a RRmod compound and additional therapeutic agent(s) can be formulated as separate compositions which are given at the same time or different times, or the therapeutic agents can be given as a single composition.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example

We discovered a new class of inhibitors that has higher selectivity for hRRM1, moving away from the nucleoside-based analogues and towards reversible, competitive, non-nucleoside inhibitors.

Figure 3:
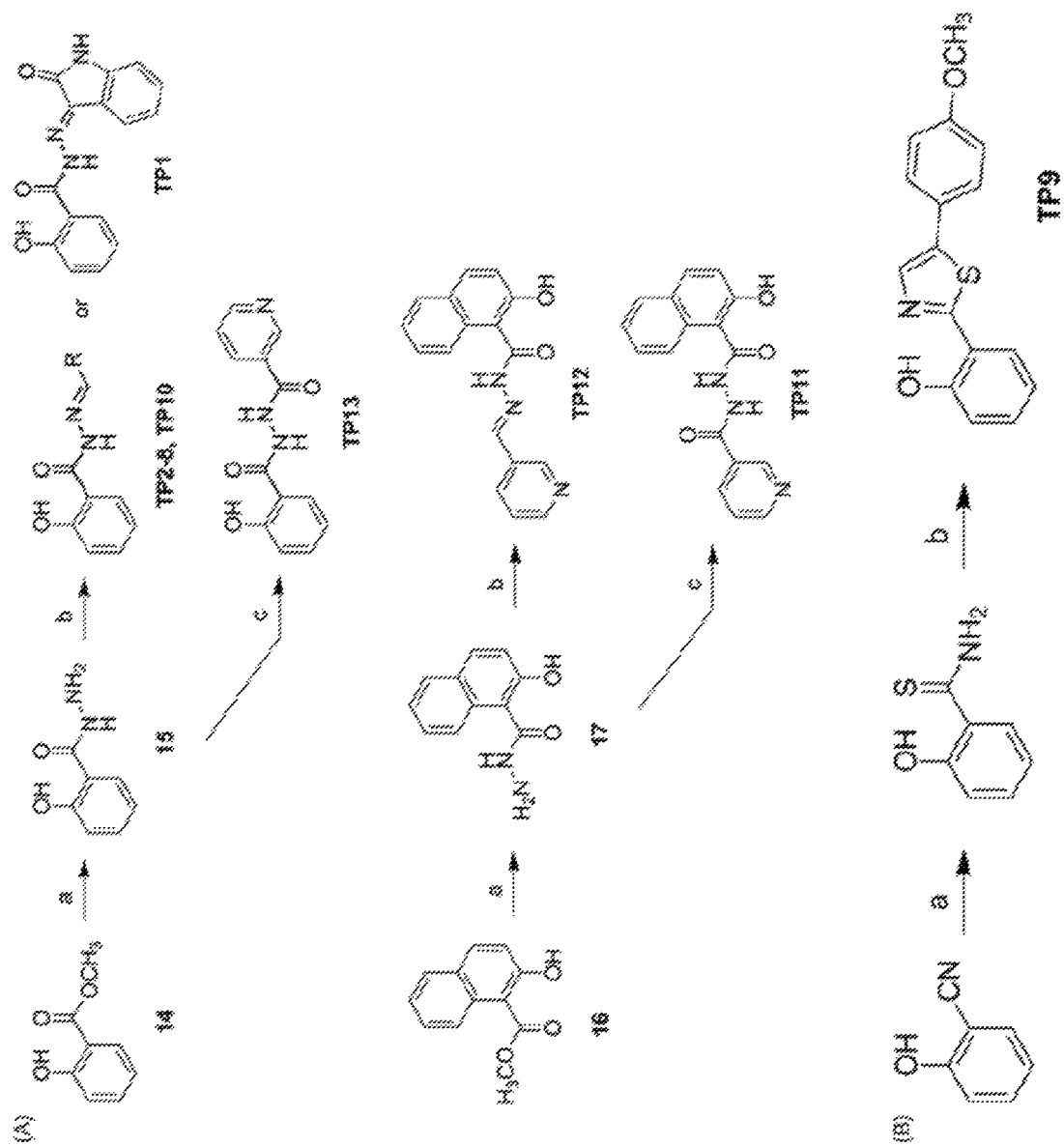
FIG. 3 illustrates a synthetic approach to compounds TP1-3.
Figure 4A:
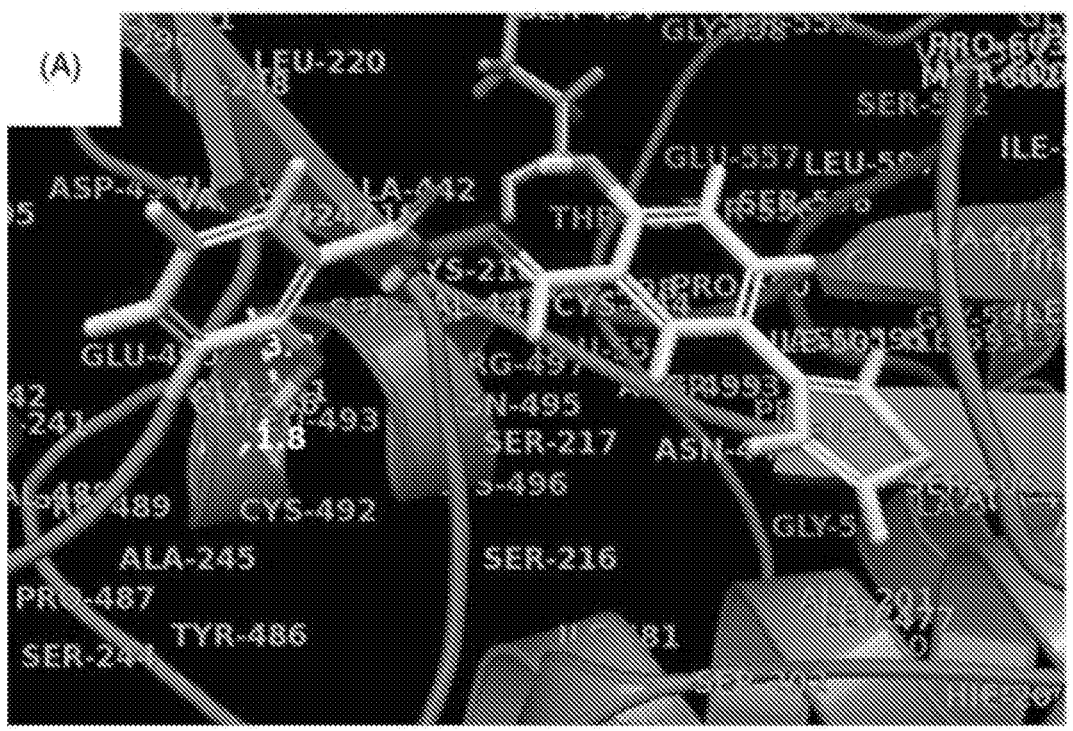
FIGS. 4(A-D) illustrate images showing predicted binding interactions of TP compounds at the C-site of hRRM1.

This example shows the structure activity relationship of the new class of compounds and the chemical diversity that can target a compound to the phosphate- and ribose-binding domains within the C-site of human ribonucleotide reductase (hRR). One structure-guided approach to this goal was to modify the naphthalene ring of our previously discovered hRR inhibitor, NSAH, by dissociating the fused ring and providing a biphenyl moiety with different types of substitutions (Group 1). Furthermore, the phenyl ring was replaced by thiophene and furan using a bioisosterism strategy (FIG. 4(A)). To understand the effect of the linker on RR modulation, the hydrazide group was replaced by diacylhydrazine or thiazole (FIG. 4(A), Group 2). Meanwhile, some polar rings such as pyridine, adenine, isatin and 2-pyridone were linked by hydrazide or diacylhydrazine to explore the structure-activity relationship. As a result, compounds TP1-13 (FIG. 3(B)) were synthesised and relevant assays to characterise their interaction with hRRM1 were conducted in this example. Using docking studies to explore possible interactions with hRRM1, it was determined that this library of compounds displayed an increase in the interactions with the phosphate-binding region of the C-site, and the best binding compounds make use of strong interactions to either the phosphate-binding region or residues near loop 2. Cancer cell studies indicated that group 1 compounds showed the greatest potency in cells, where polar substituents incorporating electronegative elements distinguished the more cytotoxic compounds. In fact, the most potent inhibitors from this class demonstrated up to a twofold improvement in potency against the growth inhibition of pancreatic cancer cells (Panc1) relative to NSAH. The results of this study will lead to the design of future generations of compounds that further improve on target hRR inhibition and cytotoxic efficacy.

Materials and Methods

Synthesis and Characterisation of TP1-13

Nuclear magnetic resonance (1H NMR and 13C NMR) spectra were recorded with Bruker Fourier 500 NMR spectrometers, with chemical shifts in parts per million (d) downfield from tetramethylsilane (TMS), the internal standard. Highresolution mass spectra (HRMS) were recorded with a JEOL (JMS-700) mass spectrometer. The purities of the final compounds were determined using an Agilent 1100 series HPLC system with a C-18 column (Agilent ZORBAX Eclipse XDB-C18 5 1m, 4.6 mm×150 mm) and were found to be >95%. Flash column chromatography was conducted using silica gel (Merck Kieselgel 60, No. 9385, 230-400 mesh ASTM). All reactions were conducted under an atmosphere of dry $N_2$.

(E)-2-Hydroxy-N'-(2-Oxoindolin-3-Ylidene)Benzohydrazide (TP1)

A mixture of methyl salicylate (1.0 eq), $N_2H_4$ (1.1 eq), and EtOH was heated to reflux until the reaction complete. The reaction mixture was filtrated and washed with EtOH to afford a white solid. The resultant was re-suspended in EtOH, and then isatin (1.1 eq) was added. The resulting mixture was heated to reflux until the reaction was complete (12 h). The reaction was quenched by adding $H_2O$ and the resulting suspension was filtered and washed by EtOH to obtain TP1 (42%). mp=320.4° C. (decomposed); $^1$H NMR (500 MHz, DMSO-$d_6$) δ 6.92 (d, J=8.0 Hz, 1H), 6.97 (t, J=8.5 Hz, 1H), 7.01 (d, J=8.5 Hz, 1H), 7.08 (t, J=8.0 Hz, 1H), 7.35 (dt, J=1.0, 8.0 Hz, 1H), 7.44 (dt, J=1.5, 8.5 Hz, 1H), 7.57 (d, J=7.5 Hz, 1H), 7.97 (dd, 1.0, 7.5 Hz, 1H), 11.13 (s, 1H), 11.64 (s, 1H), 14.35 (s, 1H). $^{13}$C NMR (125 MHz, DMSO-$d_6$) δ 111.34, 111.59, 115.75, 117.28, 117.51, 117.87, 120.14, 120.71, 120.95, 121.23, 122.35, 122.86, 124.17, 131.82, 131.85, 131.94, 133.26, 134.70, 134.93, 137.49, 139.03, 142.86, 144.35, 156.51, 157.14, 162.03, 163.36, 165.28. HRMS (ESI) for $C_{15}H_{12}N_3O_3$ $[M+H]^+$ calculated 282.0879, found 282.0880.

(E)-2-Hydroxy-N'4(4-Hydroxy-1-1,1'-Biphenyl)-3-Yl) Methylene)-Benzohydrazide (TP2)

The title compound was obtained in 63% overall yield from compound 14 in a manner similar to that described for the preparation of TP1 (reaction time: 12 h): mp=273.5-274.9° C.; 1H NMR (500 MHz, DMSO-$d_6$) δ 6.96-7.01 (m, 2H), 7.05 (d, J=8.5 Hz, 1H), 7.32 (t, J=7.5 Hz, 1H), 7.43-7.48 (m, 3H), 7.62-7.65 (m, 3H), 7.88 (d, J=2.0 Hz, 1H), 7.91 (dd, J=1.0, 8.0 Hz, 1H), 8.76 (s, 1H), 11.34 (s, 1H), 11.80-11.86 (m, 1H), 12.11 (s, 1H). $^{13}$C NMR (125 MHz, DMSO-d 6) δ 116.15, 117.54, 117.78, 119.49, 126.62, 127.34, 127.77, 129.09, 129.37, 130.37, 132.00, 134.45, 139.90, 149.23, 157.61, 159.50, 165.07. HRMS (ESI) for $C_{20}H_{17}N_2O_3$ $[M+H]^+$ calculated 333.1239, found 333.1241.

(E)-2-Hydroxy-N'-(2-Hydroxy-5-(Thiophen-3-Yl)-Benzylidene)-Benzohydrazide (TP3)

The title compound was obtained in 70% overall yield from compound 14 in a manner similar to that described for the preparation of TP1 (reaction time: 12 h): mp=282.9-284.6° C.; 1H NMR (500 MHz, DMSO-$d_6$) δ 6.96-7.01 (m, 3H), 7.46 (dt, J=1.0, 8.0 Hz, 1H), 7.52 (d, J=5.0 Hz, 1H), 7.61 (dd, J=3.0, 4.5 Hz, 1H), 7.67 (dd, J=2.0, 8.5 Hz, 1H), 7.75 (d, J=1.5 Hz, 1H), 7.88-7.92 (m, 2H), 8.72 (s, 1H), 11.33 (s, 1H), 11.86-12.08 (m, 2H). $^{13}$C NMR (125 MHz, DMSO-$d_6$) δ 116.17, 117.43, 117.78, 119.27, 119.49, 120.01, 126.47, 127.31, 127.45, 129.10, 129.97, 134.45, 141.22, 149.35, 157.24, 159.46, 165.05. HRMS (ESI) for $C_{18}H_{15}N_2O_3S$ $[M+H]^+$ calculated 339.0803, found 339.0804.

(E)-N'-(6-(Furan-3-Yl)-2-Hydroxy-3-Methoxybenzylidene)-2-Hydroxybenzohydrazide (TP4)

The title compound was obtained in 61% overall yield from compound 14 in a manner similar to that described for the preparation of TP1 (reaction time: 12 h): mp=228.3° C. (decomposed); $^1$H NMR (500 MHz, DMSO-$d_6$) δ 3.83 (s, 3H), 6.70 (s, 1H), 6.84 (d, J=8.0 Hz, 1H), 6.94-6.99 (m, 2H), 7.09 (d, J=8.5 Hz, 1H), 7.44-7.48 (m, 1H), 7.81-7.85 (m, 3H), 8.79 (s, 1H), 11.71 (s, 1H), 12.18 (s, 1H), 12.51 (s, 1H). $^{13}$C NMR (125 MHz, DMSO-$d_6$) d 56.37, 112.98, 114.89, 115.62, 115.69, 117.84, 119.38, 120.65, 123.60, 126.44, 128.73, 134.61, 141.32, 143.96, 147.82, 149.33, 150.38, 159.79, 165.18. HRMS (ESI) for $C_{19}H_{17}N_2O_5$ $[M+H]^+$ calculated 353.1137, found 353.1139.

(E)-2-Hydroxy-N'-((3-Hydroxy-4-Methoxy-11,1'-Biphenyll-2-Yl)Methylene)-Benzohydrazide (TP5)

The title compound was obtained in 58% overall yield from compound 14 in a manner similar to that described for the preparation of TP1 (reaction time: 12 h): mp=257.9-259.4° C.; $^1$H NMR (500 MHz, DMSO-$d_6$) δ 3.85 (s, 3H), 6.77 (d, J=8.0 Hz, 1H), 6.91 (t, J=7.5 Hz, 1H), 6.94 (d, J=8.5 Hz, 1H), 7.12 (d, J=8.5 Hz, 1H), 7.34-7.37 (m, 2H), 7.42-7.51 (m, 4H), 7.78 (dd, J=1.0, 8.0 Hz, 1H), 8.54 (s, 1H), 11.64 (s, 1H), 12.16 (s, 1H), 12.56 (s, 1H). $^{13}$C NMR (125 MHz, DMSO-d 6) δ 56.39, 114.70, 115.34, 115.61, 117.82, 119.31, 120.82, 127.77, 128.67, 128.91, 130.36, 134.59, 135.97, 139.53, 147.90, 149.22, 150.16, 159.84, 165.30. HRMS (ESI) for $C_{21}H_{19}N_2O_4$ [M+H]$^+$ calculated 363.1345, found 363.1347.

(E)-2-Hydroxy-N'-(2-Hydroxy-3-Methoxy-6-(Thiophen-3-Yl)Benzylidene)-Benzohydrazide (TP6)

The title compound was obtained in 75% overall yield from compound 14 in a manner similar to that described for the preparation of TP1 (reaction time: 12 h): mp=229.5° C.; $^1$H NMR (500 MHz, DMSO-d$_6$) δ 3.83 (s, 3H), 6.82 (d, J=8.5 Hz, 1H), 6.91-6.97 (m, 2H), 7.08 (d, J=8.5 Hz, 1H), 7.20 (d, J=5.0 Hz, 1H), 7.44 (dt, J=1.5, 8.5 Hz, 1H), 7.52 (d, J=1.5 Hz, 1H), 7.67 (dd, J=3.0, 5.0 Hz, 1H), 7.81 (d, J=8.0 Hz, 1H), 8.67 (s, 1H), 11.69 (s, 1H), 12.19 (s, 1H), 12.55 (s, 1H). $^{13}$C NMR (125 MHz, DMSO-d$_6$) δ 56.39, 114.72, 115.60, 115.64, 117.84, 119.35, 120.78, 124.66, 126.79, 128.71, 130.09, 130.63, 134.60, 139.82, 147.87, 149.24, 150.29, 159.83, 165.27. HRMS (ESI) for $C_{19}H_{16}N_2NaO_4S$ [M+Na]$^+$ calculated 391.0728, found 391.0731.

(E)-N'-(4-(6-Amino-9H-Purin-9-Yl)Benzylidene)-2-Hydroxybenzohydrazide (TP7)

The title compound was obtained in 33% overall yield from compound 14 in a manner similar to that described for the preparation of TP1 (reaction time: 12 h): mp=229.5° C.; $^1$H NMR (500 MHz, DMSO-d$_6$) δ 6.95-7.01 (m, 2H), 7.41-7.47 (m, 3H), 7.90-7.97 (m, 3H), 8.08 (d, J=8.5 Hz, 2H), 8.25 (s, 1H), 8.54 (s, 1H), 8.68 (s, 1H), 11.79 (s, 1H), 11.91 (s, 1H). $^{13}$C NMR (125 MHz, DMSOd$_6$) δ 116.55, 117.74, 119.46, 119.88, 123.27, 128.74, 129.13, 133.39, 134.29, 137.00, 139.87, 148.14, 149.60, 153.73, 156.86, 159.38, 165.21. HRMS (ESI) for $C_{19}H_{16}N_7O_2$ [M+H]$^+$ calculated 374.1365, found 374.1367.

(E)-2-Hydroxy-N'-((2-Hydroxynaphthalen-1-Yl)Methylene)-Benzohydrazide (TP8)

The title compound was obtained in 78% overall yield from compound 14 in a manner similar to that described for the preparation of TP1 (reaction time: 12 h): mp=223.8° C.; $^1$H NMR (500 MHz, DMSO-d$_6$) δ 6.97-7.04 (m, 2H), 7.23 (d, J=9.0 Hz, 1H), 7.38-7.42 (m, 1H), 7.46 (t, J=7.5 Hz, 1H), 7.59 (t, J=8.0 Hz, 1H), 7.87 (d, J=8.0 Hz, 1H), 7.91-7.94 (m, 2H), 8.30 (d, J=8.5 Hz, 1H), 9.54 (s, 1H), 11.93 (s, 2H), 12.73 (s, 1H). $^{13}$C NMR (125 MHz, DMSOd$_6$) δ 109.08, 116.17, 117.79, 119.37, 119.61, 121.43, 124.03, 128.21, 128.29, 129.24, 129.40, 132.18, 133.39, 134.49, 148.17, 158.62, 159.29, 164.48. HRMS (ESI) for $C_{18}H_{15}N_2O_3$ [M+H]$^+$ calculated 307.1083, found 307.1085.

2-(5-(4-Methoxyphenyl)Thiazol-2-Yl)-Phenol (TP9)

A mixture of 2-hydroxybenzonitrile (1.0 eq), 0,0-diethyl dithiophosphate (2.0 eq), and H$_2$O was stirred at 80° C. until reaction was complete (4 h). The reaction mixture was cooled, quenched with saturated NaHCO$_3$, and extracted by ethyl acetate (3 times). The organic layer was collected and dried under reduced pressure. The resulting residue was dissolved in EtOH, and then 4-methoxyphenacyl bromide (1.0 eq) was added. The mixture was heated to reflux until the reaction was complete (4 h). The solvent was removed under reduced pressure. The resulting residue was purified by recrystallization with hexane and MeOH to afford a white solid TP9 (63%). mp=95.2-96.8° C.; 1H NMR (500 MHz, DMSO-d$_6$) δ 3.84 (s, 3H), 6.94 (dt, J=1.0, 8.0 Hz, 1H), 7.00-7.03 (m, 3H), 7.33 (dt, J=1.0, 7.5 Hz, 1H), 7.64 (s, 1H), 7.77 (dd, J=1.0, 7.5 Hz, 1H), 7.84 (d, J=9.0 Hz, 2H), 11.30 (s, 1H). $^{13}$C NMR (125 MHz, DMSO-d$_6$) δ 54.41, 109.78, 113.91, 116.96, 117.10, 119.32, 126.18, 126.94, 127.10, 131.36, 154.01, 156.33, 160.15, 168.19. HRMS (ESI) for $C_{16}H_{14}NO_2S$ [M+H]$^+$ calculated 284.0745, found 284.0748.

(E)-N'-((2-Hydroxynaphthalen-1-Yl)Methylene)-4-(2-Oxopyridin-1(2H)-Yl)-Benzohydrazide (TP10)

The title compound was obtained in 40% overall yield from compound 14 in a manner similar to that described for the preparation of TP1 (reaction time: 12 h): mp=258.6° C.; $^1$H NMR (500 MHz, DMSO-d$_6$) δ 6.36 (t, J=6.5 Hz, 1H), 6.52 (d, J=9.0 Hz, 1H), 7.25 (d, J=9.0 Hz, 1H), 7.42 (t, J=7.5 Hz, 1H), 7.54 (t, J=7.5 Hz, 1H), 7.60-7.73 (m, 4H), 7.90 (d, J=8.0 Hz, 1H), 7.94 (d, J=9.0 Hz, 1H), 8.12 (d, J=8.0 Hz, 2H), 8.26 (d, J=8.0 Hz, 1H), 9.54 (s, 1H), 12.36 (s, 1H), 12.73 (s, 1H). $^{13}$C NMR (125 MHz, DMSO-d$_6$) δ 106.34, 109.02, 119.37, 121.11, 121.18, 124.04, 127.53, 128.28, 128.31, 128.89, 129.46, 132.11, 132.69, 133.31, 139.12, 141.29, 144.13, 147.63, 158.55, 161.51, 162.20. HRMS (ESI) for $C_{23}H_{18}N_3O_3$ [M+H]$^+$ calculated 384.1348, found 384.1351.

N'-(2-Hydroxy-1-Naphthoyl)-Nicotinohydrazide (TP11)

The title compound was obtained in 55% overall yield from compound 14 in a manner similar to that described for the preparation of TP1 (reaction time: 3 h): mp=227.1-228.6° C.; 1H NMR (500 MHz, DMSO-d$_6$) d 7.04 (d, J=7.5 Hz, 1H), 7.13 (d, J=8.5 Hz, 1H), 7.35 (d, J=9.0 Hz, 1H), 7.41 (t, J=7.5 Hz, 1H), 7.49 (dt, J=1.5, 9.0 Hz, 1H), 7.54 (dt, J=1.0, 8.0 Hz, 1H), 7.88 (dd, J=1.5, 7.5 Hz, 1H), 7.94 (d, J=8.0 Hz, 1H), 7.97 (d, J=8.5 Hz, 1H), 8.08 (d, J=9.0 Hz, 1H), 10.41 (s, 1H), 10.80 (s, 1H). $^{13}$C NMR (125 MHz, DMSO-d$_6$) δ 103.07, 110.14, 117.64, 118.82, 120.29, 123.72, 124.17, 128.05, 128.58, 128.97, 129.26, 132.65, 133.94, 134.20, 156.83, 157.04, 161.88, 164.22. HRMS (ESI) for $C_{17}H_{13}N_3NaO_3$ [M+Nar]$^+$ calculated 330.0855, found 330.0850.

(E)-2-Hydroxy-N'-(Pyridin-3-Ylmethylene)-1-Naphthohydrazide (TP12)

The title compound was obtained in 45% overall yield from compound 14 in a manner similar to that described for the preparation of TP1 (reaction time: 6 h): mp=202.8-204.5° C.; $^1$H NMR (500 MHz, DMSO-d$_6$) δ 7.18 (d, J=9.0 Hz, 1H), 7.31 (d, J=7.5 Hz, 1H), 7.44-7.50 (m, 2H), 7.78 (d, J=8.0 Hz, 1H), 7.82-7.86 (m, 2H), 8.22 (s, 1H), 8.35 (d, J=8.0 Hz, 1H), 8.54 (d, J=4.0 Hz, 1H), 8.85 (s, 1H). $^{13}$C NMR (125 MHz, DMSO-d$_6$) δ 114.48, 117.49, 123.11, 123.21, 124.14, 127.15, 127.92, 128.22, 130.92, 131.65, 132.00, 134.76, 145.03, 148.45, 149.99, 153.14, 166.39. HRMS (ESI) for $C_{17}H_{14}N_3O_2$[M+H]$^+$ calculated 292.1086, found 292.1088.

N'-(2-Hydroxybenzoyl)-Nicotinohydrazide (TP13)

A mixture of methyl salicylate (1.0 eq), N$_2$H$_4$ (1.1 eq), and EtOH was heated to reflux until the reaction was complete (2 h). The reaction mixture was filtered and washed with EtOH to afford a white solid. To a mixture of the resulting product (1.0 eq), K$_2$CO$_3$ (1.2 eq) and p-dioxane nicotinoyl chloride (1.2 eq) was added and the resultant mixture was heated at 40° C. until the reaction was complete (4 h). The reaction mixture was quenched with H$_2$O and extracted by ethyl acetate (3 times). The organic layer was collected, dried over MgSO$_4$, and filtered. The resulting filtrate was dried under reduced pressure to obtain TP13 as a white solid (75%). mp=216.6-217.7° C.; 1H NMR (500 MHz, DMSO-d$_6$) δ 6.95-7.00 (m, 2H), 7.46 (t, J=7.5 Hz, 1H), 7.57 (dd, J=5.0, 8.0 Hz, 1H), 7.92 (d, J=7.0 Hz, 1H), 8.26 (d, J=8.0 Hz, 1H), 8.78 (d, J=4.0 Hz, 1H), 9.08 (d, J=1.0 Hz, 1H), 10.73 (s, 1H), 10.90 (s, 1H), 11.83 (s, 1H). $^{13}$C NMR (125 MHz, DMSO-d$_6$) δ 115.18, 117.84, 119.59, 124.19, 128.51, 128.94, 134.66, 135.75, 148.93, 153.06, 159.53, 164.62, 167.91. HRMS (ESI) for $C_{13}H_{12}N_3O_3$[M+H]$^+$ calcd 258.0879, found 258.0880.

Compound Preparation and Solubility Determination

For each compound, stock solutions were made in 100% DMSO to assure full solubility. Spectra of standard solutions in 100% acetonitrile were taken using UV spectroscopy. An extinction coefficient was calculated from the plot of the absorbance vs drug concentration using Beer's law.

$K_D$ values were determined in $K_D$ buffer [50 mM TRIS, pH 8.0, 5 mM $MgCl_2$, 5% glycerol and 10 mM DTT]. Because the solubility of the compounds was limited in this buffer, the solubility was empirically determined as follows. Increasing amounts of a compound were dissolved in 1.5 ml of $K_D$ buffer. The solutions were mixed by vortex and centrifuged at 5000 lag for 10 mM, and the supernatant was promptly removed and absorbance measured by UV/Vis spectrophotometry. Using the extinction coefficients, the concentration of soluble drug was calculated for each total concentration. Drug solubility measurements were carried out in duplicate. P lots of measured vs predicted concentrations were plotted in Origin graphing software. Samples having precipitates that did not pellet were excluded from the list of 13 compounds examined in this manuscript.

Protein Expression and Purification of hRRM1

The hRRM1 protein was expressed in *Escherichia coli* B121-codon plus (DE3)-RIL cells and purified using a peptide affinity column, as previously described in Fairman et al. The homogenous protein was pooled and concentrated to 0.2 mg/mL, quantified using UV spectroscopy.

$K_D$ Determination by Fluorescence Quenching

The dissociation constant ($K_D$) was measured for each of the compounds using a tryptophan florescence quenching assay, as described previously with hRRM1 at 0.2 mg/mL. Tryptophan florescence spectra of hRRM1 were measured using a Horiba Fluoromax-4, 1155D-3113 FM spectrophotometer after exciting the sample at 295 nm. A background spectrum was recorded with protein in $K_D$ buffer followed by the incremental addition of compounds (0-150 mM) at room temperature. The data were fitted in Origin graphing software using a quadratic form of the equilibrium binding equation $$y = \frac{(c + x + k) - ((c + x + k))2 - \sqrt{4cx}}{2c},$$

where A is the amplitude of the reaction, c is the concentration of enzyme, x is the substrate concentration, y is the percent of fluorescence quenching and K is the $K_D$. Measurements were made in duplicate to estimate error. $K_D$'s were corrected for the measured concentration of soluble compound from the concentration of total added compound. Error of the corrected $K_D$'s were calculated using the error propagation equation $$\frac{\sigma_x}{X} = \sqrt{\left(\frac{\sigma_a}{a}\right)2 + \left(\frac{\sigma_b}{ab}\right)2}$$

where rx is the error of the corrected $K_D$, x is the corrected $K_D$, ra is the error of the slope of the drug concentration plot, a is the slope of the drug concentration plot, rb is the error of the measured $K_D$ and b is the measured $K_D$.

Cancer Cell Line Growth Inhibition Assay

Growth inhibition assays were performed in the Translational Research Shared Resource of the Case Comprehensive Cancer Centre. Human pancreatic cancer cells (Pancl) were maintained in standard growth medium consisting of (RPMI1640+10% FBS+2 mM glutamine+100 U/mL penicillin, and 100 mg/mL streptomycin). Cells were monitored and shown to be negative for *mycoplasma* contamination using the *Mycoplasma* Detection kit (MycoAlert™, Lonza, Basel, Switzerland). For growth inhibition assays, cells were harvested by trypsinisation and seeded into 96-well tissue culture plates at 2500 cells/mL. The following day, triplicate wells were treated with an appropriate volume of 5x-inhibitor-containing medium. The cells were cultured for 3 additional days at 37° C. in a 5% $CO_2$ humidified incubator. Cell growth was assessed by measuring total DNA content per well using an adaptation of the method of Labarca and Paigen.

In Silico Docking Studies

In silico docking of the compounds was performed using the Glide module of the Schrödinger 2017-3 modelling software suite as previously described. The docking site for the C-site was defined as a 5 Å box centred on the lead compound NSAH (TP8) bound to the hRRM1 (PDB code STUS). Compounds were docked to the C-site using Glide SP. Hits were scored by a glide scoring function and examined for their interactions with the Csite residues using Maestro.

Results

Rationale for Compound Design and Synthesis

Figure 4B:
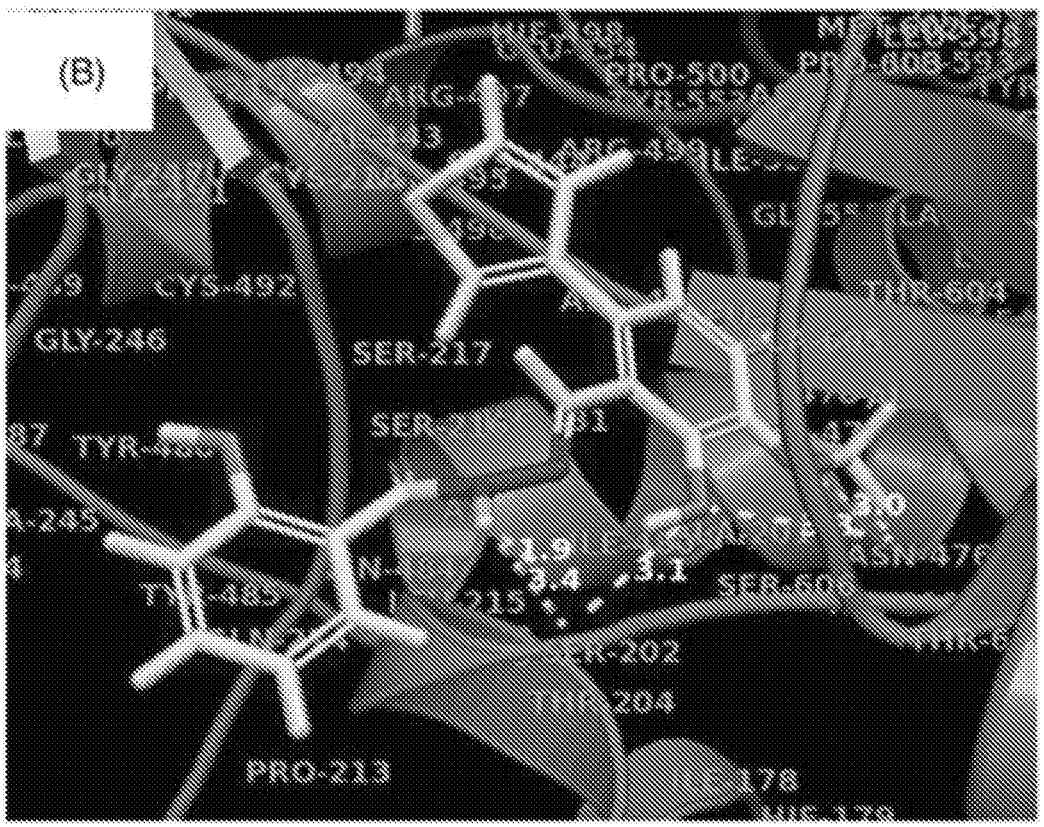
Figure 4C:
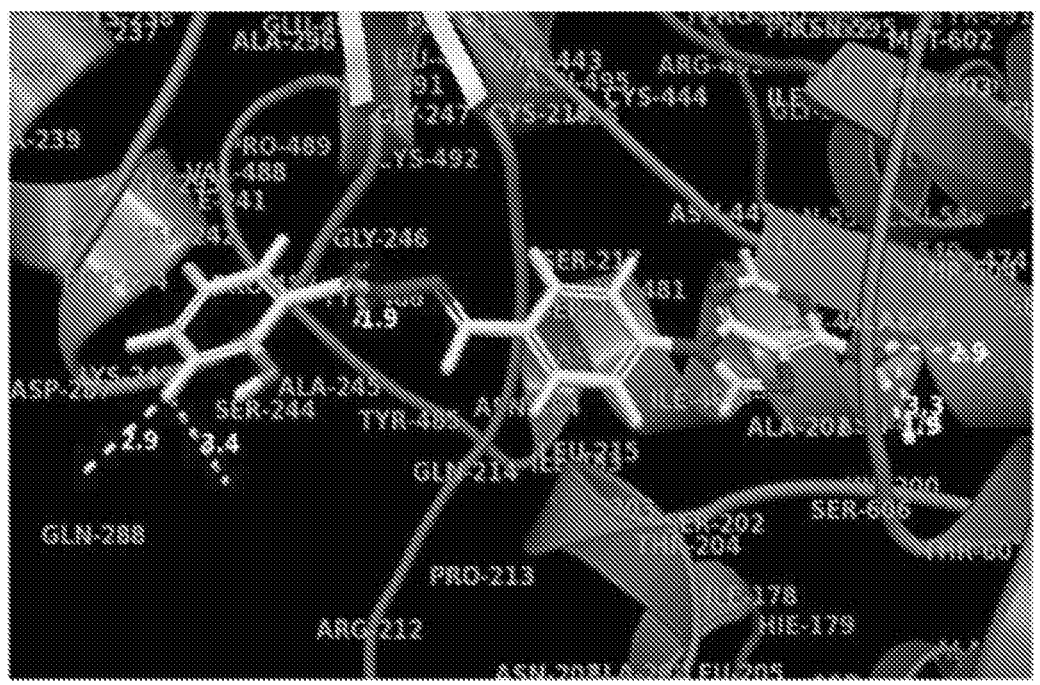
Figure 4D:
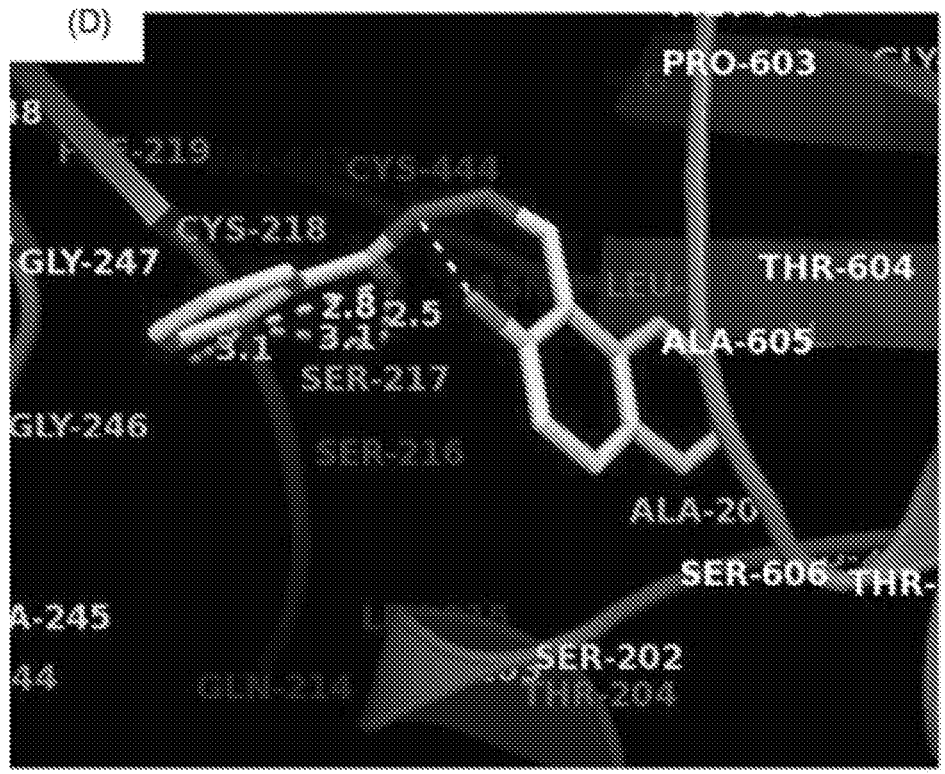

Our previous study identified NSAH (TP8), containing a 2-hydroxybenzohydrazide moiety, as an RR modulator. Its structure contains three parts, namely: 2-hydroxybenzoyl group, hydrazide linkage, and naphthalene ring. In order to understand structure-activity relationships, specifically the influence of the hydrazide moiety, we designed diacylhydrazine-containing TP11 and TP13 and thiazole derivative TP9 (FIG. 3(B)). Furthermore, hydrazide derivatives (TP1-8, TP10 and TP12) linked with biaryls or various heterocycles were also designed. Their syntheses are illustrated in FIGS. 4 and 4B. Methyl salicylate (14) was reacted with hydrazine to obtain 2-hydroxybenzohydrazide (15) which was subjected to reaction with various aldehydes or isatin to give the corresponding products TP1-8 and TP10 (FIG. 3(B)). Methyl 2-hydroxy-1-naphthoate (16) underwent a similar synthetic route to afford compound TP12 (FIG. 3(B)). Meanwhile, the reaction of 15 and 17 with nicotinoyl chloride yielded, respectively, compounds TP13 and TP11, which possess a diacylhydrazine linkage (FIG. 3(B)). The reaction of 2-hydroxybenzonitrile (18) with O,Odiethyl dithiophosphate, which generated the corresponding thioamide product, was followed by cyclisation with 4-methoxyphenacyl bromide to furnish compound TP9. These analogues were designed to enhance interactions with the C-site (FIG. 1).

In Silico Compound Docking Interactions with hRRM1

Potential interactions of TP1-13 with hRRM1 were investigated using the Schr€odinger docking software suite glide. A hRRM1 dimer with lead compound NSAH bound to the C-site (PDB ID: STUS) was used as a model for the docking of the new compounds. It was assumed that the primary site of binding for these compounds would be the C-site, because NSAH and all previously studied derivatives of NSAH have demonstrated a preference for the C-site. Our studies showed that compounds TP2-7, 9-10 are longer and therefore extend beyond NSAH, allowing for the possibility of more interactions FIG. 4(A-D). TP3 was not predicted to bind well to the phosphate-binding site in comparison to other new compounds (FIG. 4(A)). However, docking predicted it to have an increase in the number of strong interactions closer to the loop 2 region. TP7 was unique in that it was predicted to interact strongly in the phosphate-binding site with the residues: Thr607, Ser448, Ser606, and near the loop 2 region with residues: Pro294, Ala245, as well as to a residue to which NSAH exhibits strong hydrogen bonding (Ser217) (FIG. 4(C)). This is partly because TP7 extends to the outer extremities of the catalytic site (C-site). Thus, for all compounds except TP3, there was either an increase in the number of predicted C-site interactions and/or an increase in the number of strong binding interactions to the phosphate-binding site of the Csite, in comparison to the interactions that NSAH makes (FIGS. 4(A-D)).

Figure 5A:
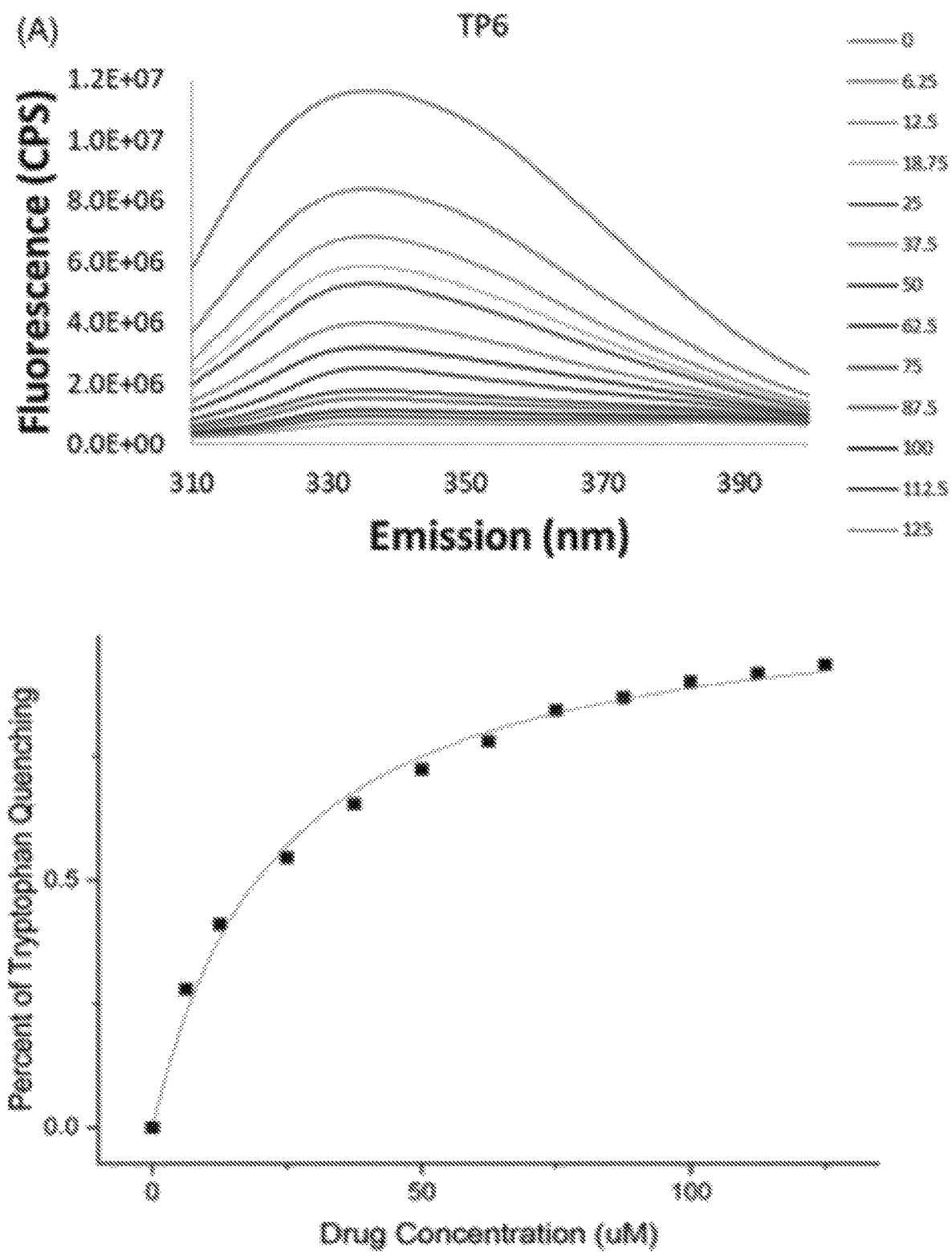
FIGS. 5(A-C) illustrate plots showing quenching of tryptophan fluorescence of hRRM1 by TP ligands.
Figure 5B:
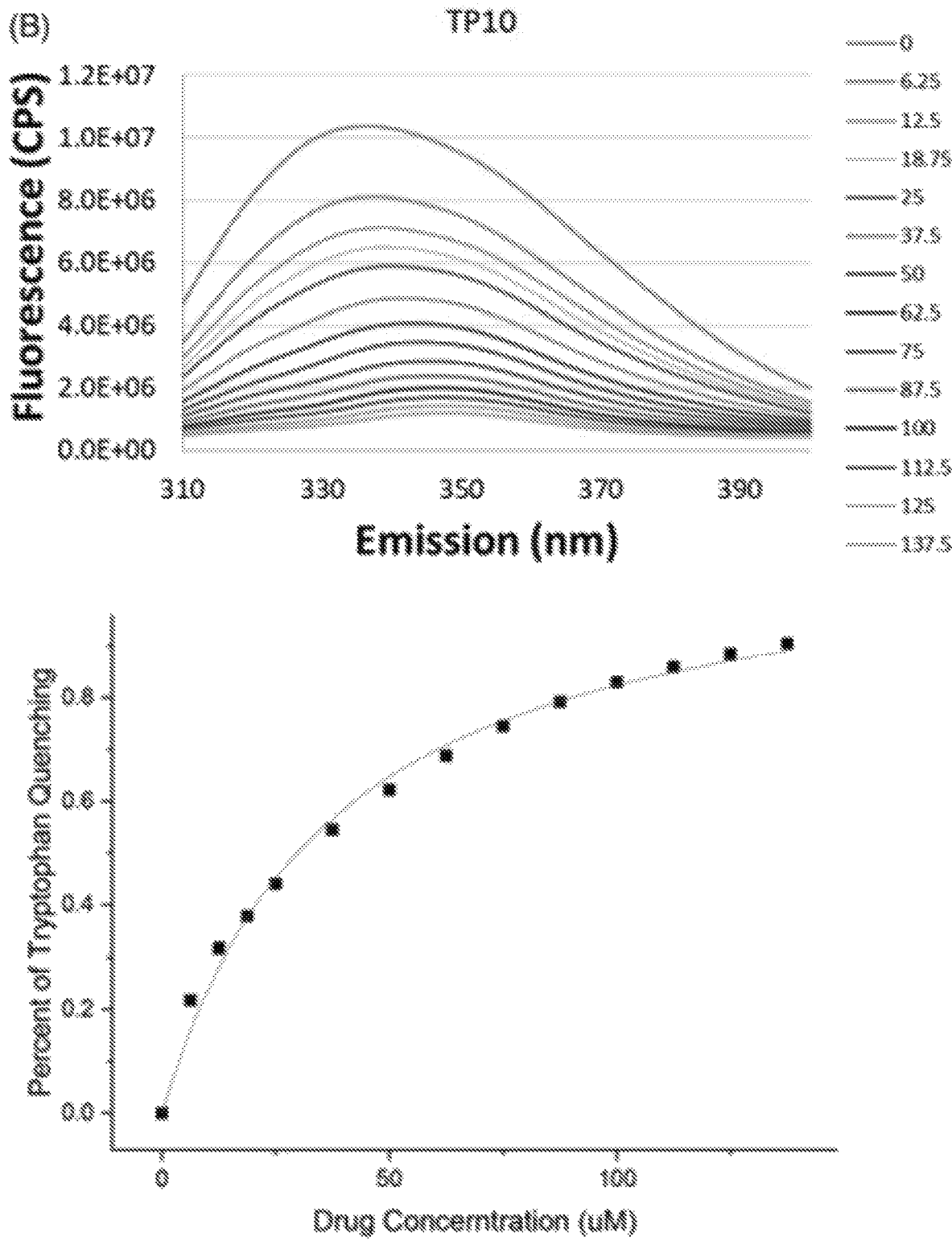
Figure 5C:
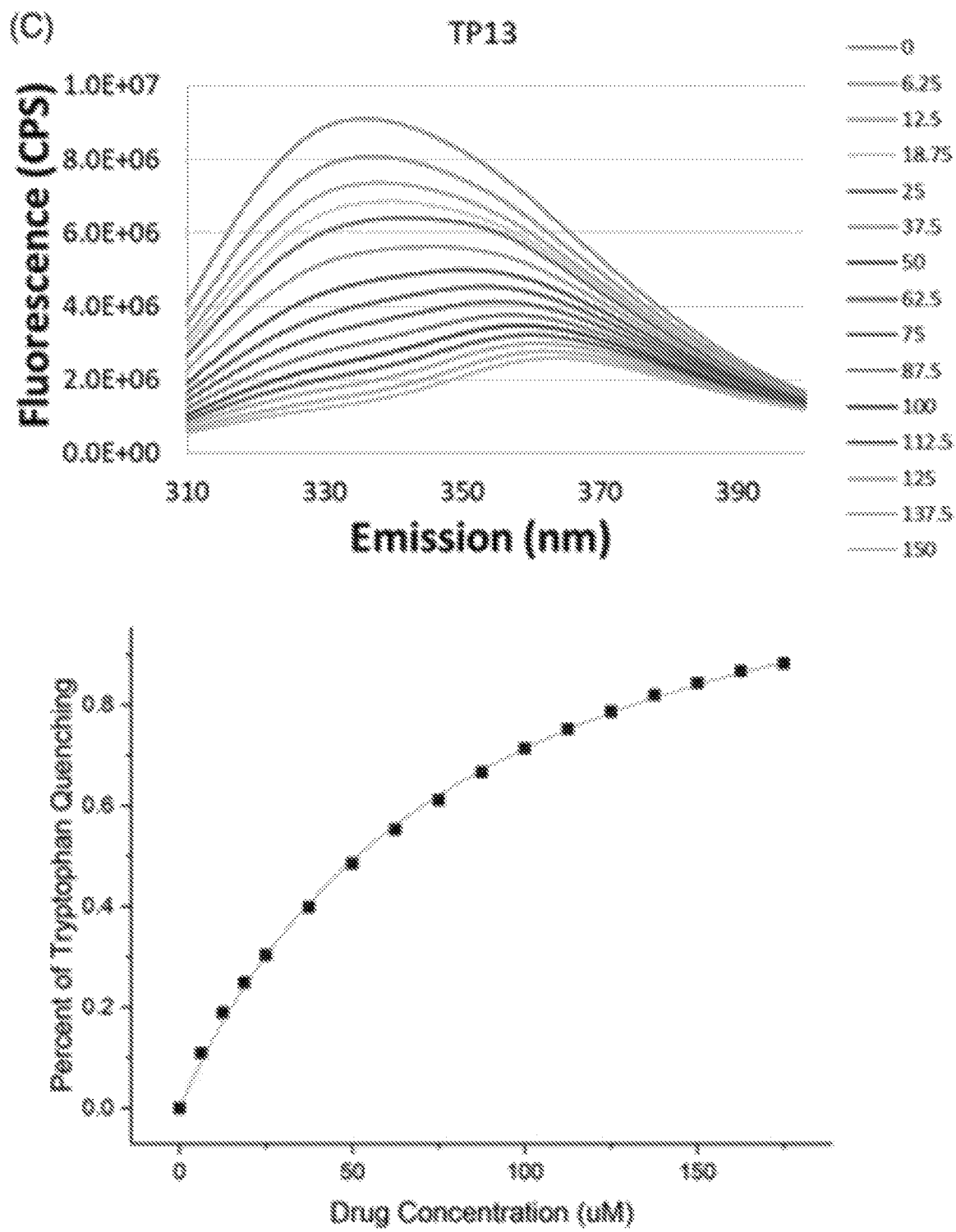
Figure 6:
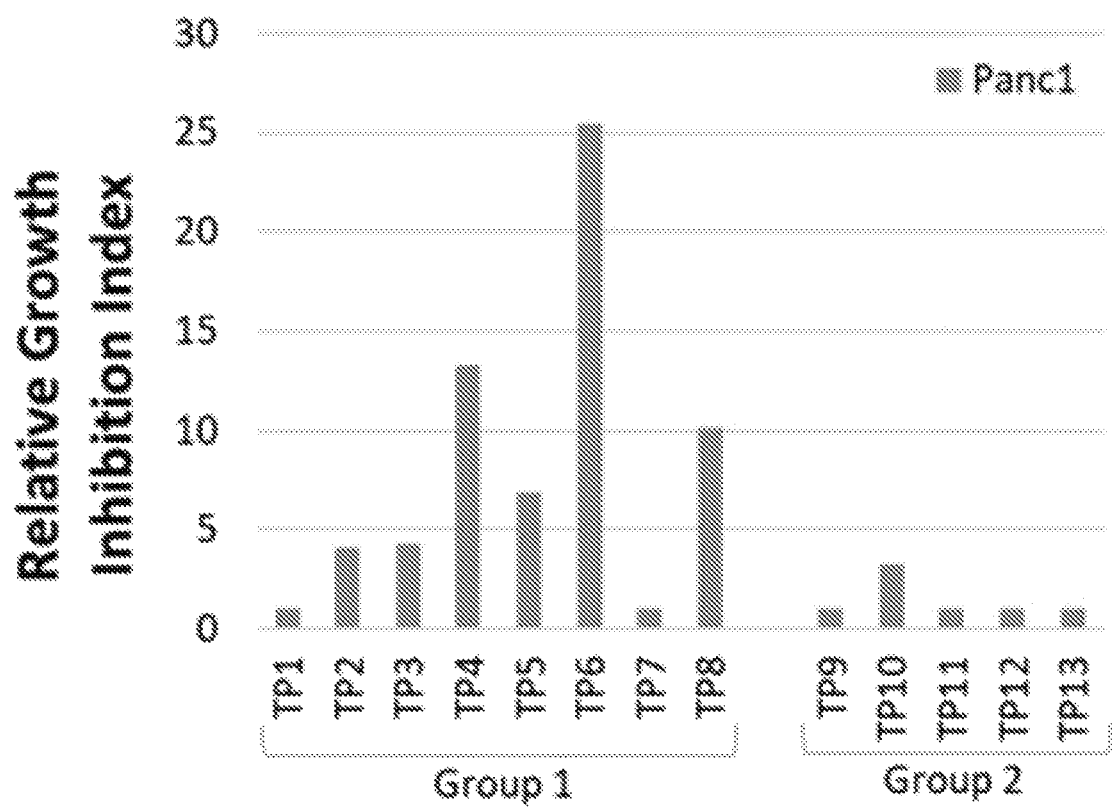
FIG. 6 illustrates a graph showing cancer growth-inhibitory activity of Panc1 pancreatic cancer cell line by TP compounds.
Figure 7:
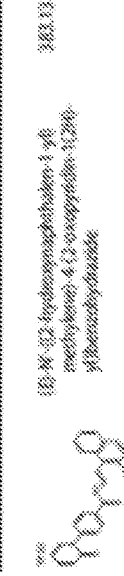
FIG. 7 illustrates a table showing experimental data.

Investigation of Compound Binding to hRRM1 Using Intrinsic Tryptophan Fluorescence TP1-13 were analysed for their ability to bind to hRRM1 and therefore quench its intrinsic tryptophan fluorescence. Using the criterion that ligands quenching at least 25% of the fluorescence have sufficient affinity for hRRM1, TP1-13 were characterised as binders of hRRM1. TP1, 4, 6, 7, 10, and 12 quenched at least 90% of the tryptophan fluorescence (FIG. 5(A-B)). TP2, 5, 8, 9, 11, and 13 each quenched approximately 80% (FIG. 5(C)), and TP3 quenched approximately 70% of tryptophan fluorescence. While percentage of quenching indicates the ability of a compound to bind to the enzyme, measuring the concentration of a compound needed to quench the fluorescence by half provides the $K_D$, a measure of the affinity of a compound for the enzyme. Corrected $K_D$'s (see Methods) ranged from 2.9±0.39-22.0±5.67 mM, where all of the new compounds have a lower $K_D$ than NSAH (22.0±5.67 mM) (FIG. 7). The reduction in the $K_D$ indicates that the chemical modifications targeting the phosphate-binding site and loop 2 resulted in better binding to hRRM1 as compared to NSAH Inhibition of Growth of Panc1 Pancreatic Cancer Cells Since gemcitabine is a core component of the current standard of care for pancreatic cancer, and we hoped to improve upon the therapeutic index for drugs treating this disease, we selected Panc1, a cell line derived from pancreatic cancer, for the study of the new compounds. Panc1 cells growing in 96-well plates were exposed to each compound continuously for three days, after which DNA content per well was measured as an indicator of cell growth. As shown in FIG. 6 and FIG. 7, TP1, 7, 9, 11, 12, and FIG. 4. Predicted binding interactions of TP compounds at the C-site of hRRM1. 13 did not inhibit the growth of Panc1 cells, even at concentrations of 10 mM. Compounds TP2, 3, and 10 showed moderate growth inhibition with $IC_{50}$'s between 2 and 3 mM (FIG. 6 and FIG. 7). Compounds TP4-6, and 8 were the most potent against this cell line, with $IC_{50}$'s below 1.5 mM (FIG. 5 and FIG. 7). Overall, the results indicated that some compounds in group 1 have marked activity against the growth of Panc1 cells, whereas group 2 is mostly ineffective (FIG. 5 and FIG. 7). TP6 demonstrated the greatest potency, with over a 2-fold decrease in $IC_{50}$ over the lead compound NSAH (TP8) (FIG. 6 and FIG. 7). A few of the compounds were also studied in other cell lines (A549 and HCT-116), showing similar potency as in Panc1 cells. This finding suggests that these compounds do not target Panc 1 cells specifically, but may be universally active against cancer cells, as would be expected since RR is found in all cells.

It was determined that replacing the phenol with polar substituents in the ortho position achieved the best activity against hRR. Replacement of the naphthalene with an indole provided similar activity. It was concluded that these derivatives favoured the C-site, just like NSAH, and all derivatives that showed improved activity against hRR in comparison to NSAH had increased interactions in the phosphate-binding site. However, these compounds had limited cellular activity.

Using the co-crystal structure of NSAH bound at the C-site of hRRM1 and its interactions (PDB code 5TUS) as a template in the present study, a small library of compounds was designed to increase the interactions with the C-site (FIG. 4). It was anticipated that improved interactions would strengthen the specificity towards hRR and reduce off-target binding. The library consists of two distinct groups. For the Group 1 compounds, the naphthalene of NSAH was replaced in anticipation of creating more interactions with the residues that are important in binding the phosphates of the natural substrates (termed phosphate-binding site). For the Group 2 compounds, the hydrazine linker was modified and polar groups were added to these linkers. In order to determine how these modifications affected interaction with hRR, computational docking and experimental assays were conducted.

To determine the extent of binding of these compounds to the hRRM1 subunit, quenching of the fluorescence of the internal tryptophans of hRRM1 was measured. The $K_D$'s ranged from 2.9±0.39-22.0±5.67 mM, indicating that all of the modified compounds bind more tightly than does NSAH ($K_D$-22.0±5.67 mM) (FIG. 7). Examination of the docking of these compounds suggests that the overall decrease in $K_D$ is influenced by the predicted increase in interactions with the phosphate-binding site within the C-site of hRRM1 compared to the binding of NSAH. With the exception of TP3, all other analogues have stronger interactions with the phosphate-binding site than NSAH (FIGS. 4(B-D)). Apart from the increase in binding to the phosphate-binding region, no other single binding characteristic explains the trends in relative affinity seen with these 13 compounds; rather, a collection of interactions contribute to the observed binding pattern. All of the compounds with a $K_D$ less than 6.2 mM are predicted to make at least one strong hydrogen bond that could contribute to the tight binding to hRRM1. Within this group, TP7 and 11 are predicted to have the most hydrogen bonds, leading to stronger binding to hRRM1 (FIG. 4(C)). TP7 has hydrogen bonds scattered throughout the length of the compound, interacting with the phosphate-binding site, at Cys218 and Ser217, and near loop 2 (FIG. 4(C)). Our previous predictions for optimising interactions at the phosphate-binding site and with loop 2 appears to be validated by this study. TP11 and 13 are the only compounds in this library that have a linker composed of single bonds, allowing for free rotation (FIG. 4(B)). With a few exceptions, compounds with a $K_D$ less than 9.4 mM form multiple predicted hydrogen bonds. TP3 is one of the exceptions, making fewer strong interactions than NSAH, and not interacting with the phosphate-binding site (FIG. 4(A)). TP3's lack of interactions with the phosphate-binding site is compensated by stronger interactions near loop 2. The trend that emerges from the study of this library is that the best hRRM1 binding compounds are either small and flexible (TP1, 11, 13) or long enough to reach loop 2 and/or the phosphate-binding site (TP3-7). Both of these groups of compounds' options contain polar substituents, but there is a limit to the benefit of size and polarity, because some of the larger molecules had low solubility in the aqueous medium of the fluorescence assay.

A common challenge in drug development is that interaction with a target and inhibitory activity against a cell-free enzyme does not always predict how the drug will perform when tested in a cell or animal model. Thus, another approach we employed was to query the structures of the compounds in our library using QikProp, an algorithm of the Schrëodinger suite to predict the cell permeability of these compounds in Caco-2 and MDCK cells (FIG. 7). With some exceptions, the algorithm was useful in predicting which compounds might be the most effective against Panc 1 cells. With the exception of TP1 and 7, group 1 had the greatest potency in Panc1 cells with $IC_{50}$'s below 2.5 mM (FIG. 6 and FIG. 7). TP6, which had the greatest potency, had the greatest predictable permeability for both Caco-2 and MDCK cells within the top seven compounds (FIG. 7). TP4-6 and 8 have similar predicted permeabilities, with the exception of TP6, which has a greater permeability for MDCK cells (FIG. 7). The compounds with $IC_{50}$'s between 2 and 3 mM are predicted to be less permeable than TP4-6 and 8 (FIG. 7). Out of the compounds that had cellular $IC_{50}$'s greater than 10 mM (TP1, 7, 9, 11-13) only T9 and 12 had good predicted permeability, even greater than that of TP6 (FIG. 7). These results suggest that theoretical prediction of permeability does not always predict activity in cells. The lack of activity against cells could be due to an assortment of factors, including poor cell permeability, drug metabolism in the cell rendering them inactive, or being good substrates for efflux pumps.

TP4-6, which were the most potent against growth of Panc1 cells, have very similar structures (FIG. 4(B)). These compounds maintain the phenol and the hydrazine linker of NSAH, but in place of the naphthalene is a guaiacol methoxyphenol linked to a furan, benzene, or thiophene. The docking of these compounds to the hRRM1 C-site provides evidence that they bind similarly to each other, revealing the importance of this modification. To further examine this modification and its contribution to enhanced binding and cellular potency, TP2 and 3 were compared. TP2 and 3 mimic TP5 and 6, respectively, but lack the methoxy group on the guaiacol methoxyphenol (FIG. 3(B)). The removal of the methoxy appears to cause over a 2-fold decrease in potency in cells as well as the loss of a similar docking pattern (FIG. 4(A) and FIG. 7). TP9, which contains a methoxy group on a benzene ring, is not only ineffective in Panc1 cells but also has a completely different predicted pattern of binding to the C-site (FIG. 6, FIG. 7). This suggests that methoxylation of the benzene ring aids in improving cell and enzyme potency but acts in concert with other polar entities. The addition of the hydroxyls as well as the polar rings aids in the increase in potency. Considering the effects of TP4-6 in the cells, it might be suggested that a polar ring with an electronegative element might further increase the relative potency.

It is well known that phenolics have potentials for being chemotherapeutic agents; however, these compounds often have poor bioavailability in vivo. Typically, phenolics are easily oxidised, leaving them vulnerable to chemical degradation or bacterial decomposition in the GI tract, most commonly by glucuronidation and sulphation. TP1-8,13 contain phenolic acids, which proposes a risk of poor bioavailability when administered in vivo, eliminating an oral administration and restricting it to IV administration. As an oral compound is more desirable for patients for its ease of use, it might be beneficial to modify these compounds if they exhibit poor bioavailability in mouse studies. Modifying these compounds by converting the phenolic to esters or ethers might produce a pro-drug and increase the bioavailability of the phenolic metabolites.

A PAINS filter (http://cbligand.org/PAINS/), which is a now well-defined way to identify the presence of potentially problematic functional groups in analogue design, was used on our compound library. Despite our lead compound, NSAH, being a potential PAINS candidate, our studies have validated this compound as an RR inhibitor binding to the C-site of hRR1 and inhibiting RR in cells. This validation adds confidence that TP1-13 would bind to the hRR1 C-site as docking to this site displayed favourable poses and possibly inhibits RR in cells. When developing compounds against RR, there is always a concern that these compounds contain chelating properties that may affect the Fe and free radical housed in the small subunit, a crucial element needed for the activity of RR. There have been many reports of agents that inhibit RR by this mechanism. As this was a concern, NSAH was tested for its ability to chelate metals. Results indicated that NSAH does not chelate $Fe^{3+}$, the iron form present in RR, up to concentrations of 5 mM nor does it bind or sequester $Mg^{2+}$ ions, which are also critical for RR activity. As these concerns are not an issue for the lead compound NSAH, we predict that these will not be an issue with TP1-13 either.

It is generally understood that targeting RR for cancer therapeutics is a challenging task as RR is present in all cells, normal and malignant. We have previously shown that the lead compound NSAH (TP8) was much less effective against blood progenitor cells than against cancer cell lines, demonstrating that NSAH has a higher therapeutic index than gemcitabine in the same cellcell comparison. This suggests that NSAH has selective activity in malignant cells, exploiting the greater proliferation in cancer cells. Accordingly, the new class of inhibitors designed from NSAH provide a superior, safer anticancer treatment. Results from this example indicate that replacing the naphthalene ring of NSAH with other cyclic ring structures containing methoxy and polar constituents results in analogues with superior activity against cancer cells.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having Described the Invention, the Following is Claimed:

1. A method of inhibiting ribonucleotide reductase activity in a neoplastic cell comprising administering to the cell an amount of a ribonucleotide reductase allosteric modulator (RRmod), wherein the RRmod has a structure selected from the group consisting of:

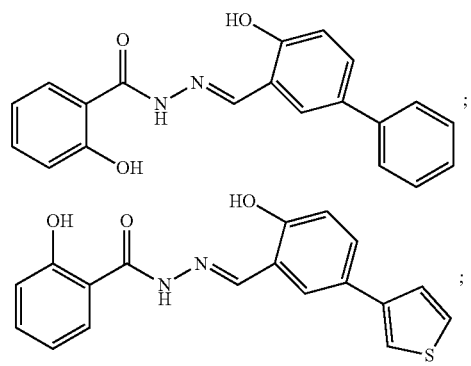

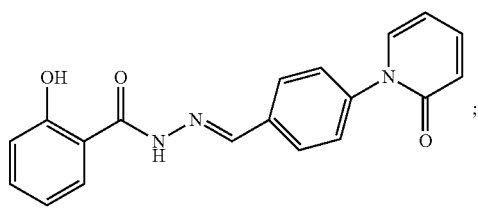

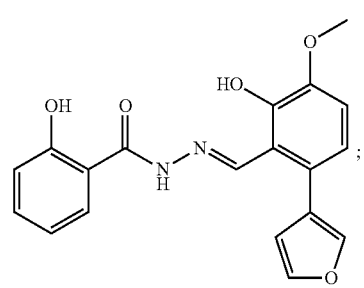

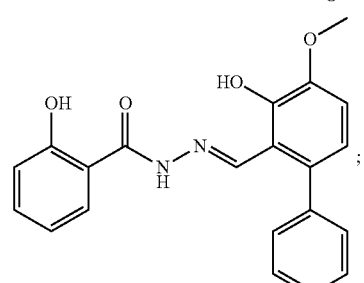

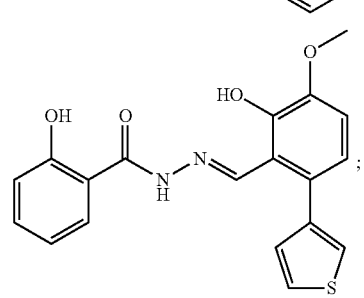

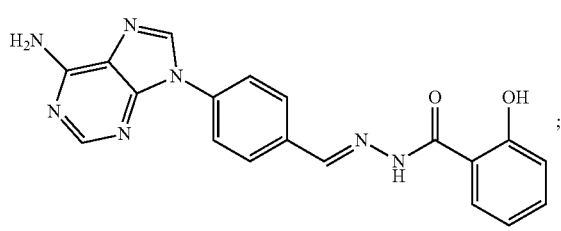

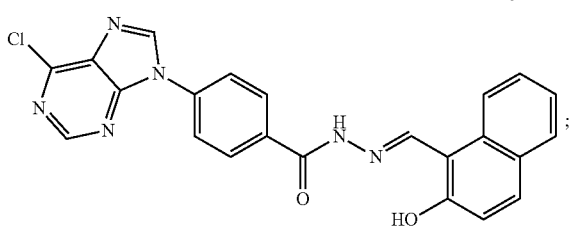

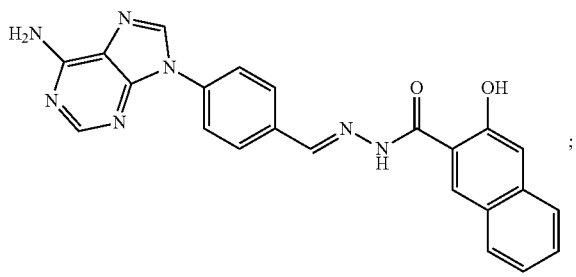

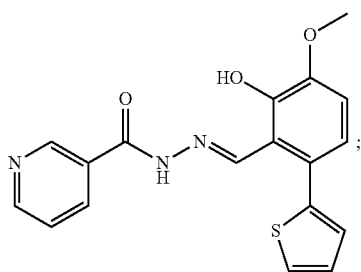

pharmaceutically acceptable salts, tautomers, and solvates thereof.

2. The method of claim 1, wherein the cell includes a cancer cell.

3. The method of claim 2, wherein the cancer cell includes a pancreatic, breast, lung, colon or glioblastoma cancer cell.

4. A method of inhibiting ribonucleotide reductase activity in a subject having a neoplastic disorder comprising:

administering to neoplastic cells of the subject a therapeutically effective amount of a pharmaceutical composition, the composition comprising a ribonucleotide reductase allosteric modulator (RRmod), wherein the RRmod has a structure selected from the group consisting of:

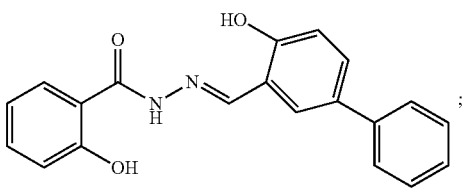

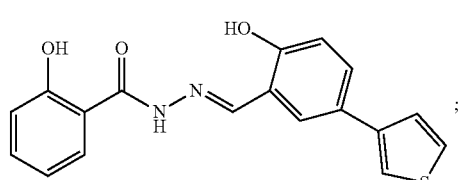

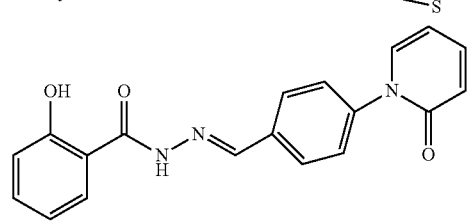

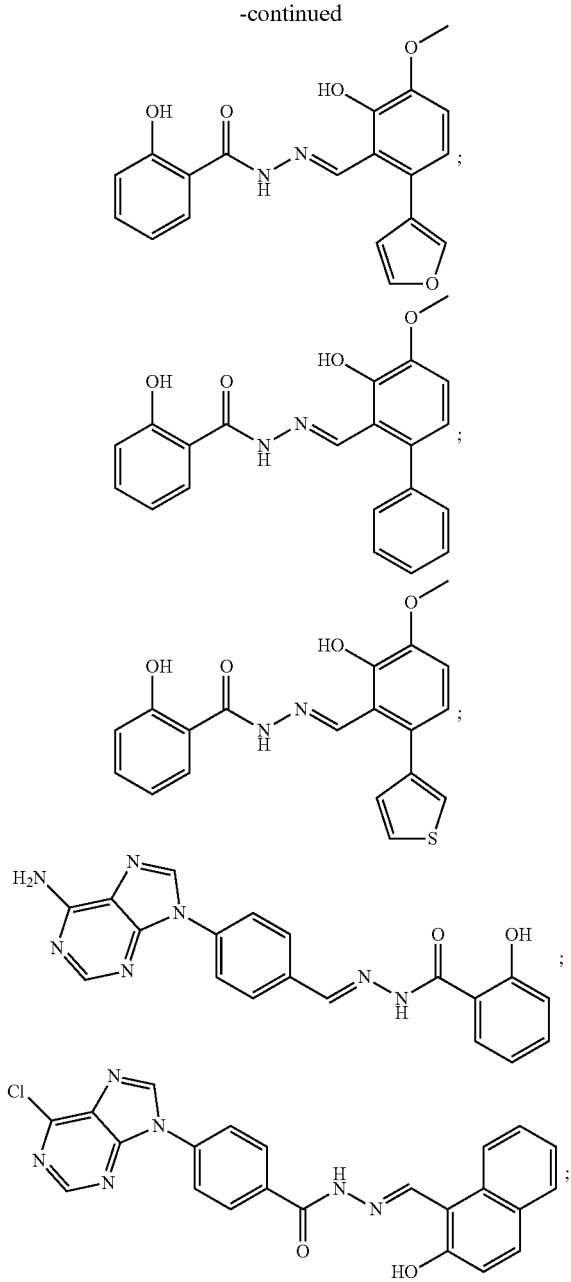

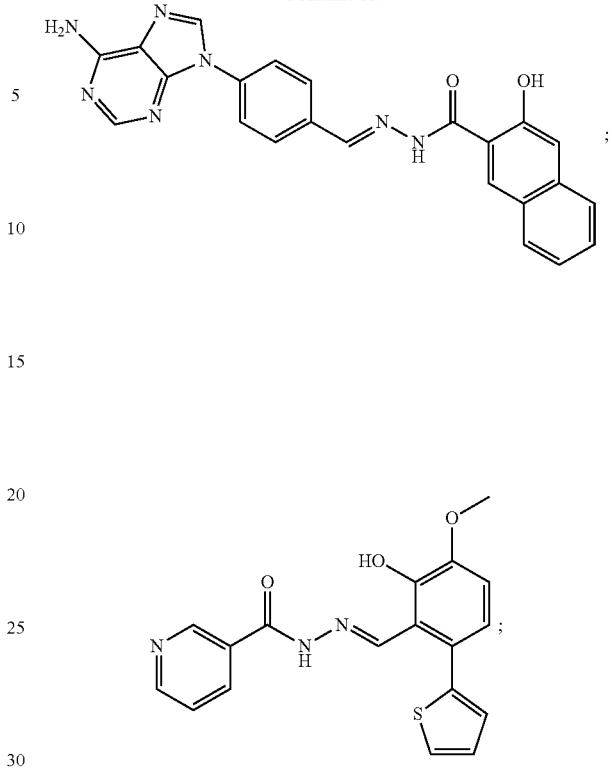

pharmaceutically acceptable salts, tautomers, and solvates thereof.

5. The method of claim 4, wherein the neoplastic disorder is a cancer.

6. Method of claim 5, wherein the cancer is pancreatic, breast, lung, colon or glioblastoma cancer.

7. The method of claim 4, wherein the method comprises further administering another therapeutic agent in conjunction with the RRmod.

8. The method of claim 7, wherein the other therapeutic agent is at least one of a chemotherapeutic agent, an antimetabolite, a DNA damaging agent, a ribonucleotide reductase inhibiting agent, an antitumorgenic agent, an antimitotic agent, an antiviral agent, an antineoplastic agent, an immunotherapeutic agent, and a radiotherapeutic agent.

* * * * *